(12) United States Patent
Branch

(10) Patent No.: US 11,197,449 B2
(45) Date of Patent: Dec. 14, 2021

(54) PEANUT VARIETY 'GEORGIA-18RU'

(71) Applicant: University of Georgia Research Foundation, Inc., Athens, GA (US)

(72) Inventor: William D. Branch, Tifton, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 44 days.

(21) Appl. No.: 16/713,720

(22) Filed: Dec. 13, 2019

(65) Prior Publication Data

US 2021/0176938 A1 Jun. 17, 2021

(51) Int. Cl.
*A01H 6/54* (2018.01)
*A01H 5/10* (2018.01)

(52) U.S. Cl.
CPC .............. *A01H 6/541* (2018.05); *A01H 5/10* (2013.01)

(58) Field of Classification Search
CPC .................................. A01H 5/10; A01H 6/541
See application file for complete search history.

(56) References Cited

U.S. PATENT DOCUMENTS 8,178,752 B1 * 5/2012 Tillman ................... A01H 5/10
800/298

OTHER PUBLICATIONS

Branch, W. D. "Registration of 'Georgia-18RU' Peanut." Journal of Plant Registrations 13.3 (2019): 326-329. (Year: 2019).*
Branch, W.D. (2007), Registration of 'Georgia-06G' Peanut. J. Plant Reg., 1: 120-120. https://doi.org/10.3198/jpr2006.12.0812crc (Year: 2007).*

* cited by examiner

*Primary Examiner* — Lee A Visone
(74) *Attorney, Agent, or Firm* — Klarquist Sparkman, LLP

(57) ABSTRACT

Herein provided is a new runner-type peanut variety designated 'Georgia-18RU' as well as the seeds, plants and derivatives of the new peanut variety 'Georgia-18RU'. Also provided are tissue cultures of the new peanut variety 'Georgia-18RU' and the plants regenerated therefrom. Methods for producing peanut plants by crossing the new peanut variety 'Georgia-18RU' with itself or another peanut variety (such as another runner-type peanut variety) and plants produced by such methods are also provided. 'Georgia-18RU' is a unique runner-type peanut cultivar having a combination of high level of tomato spotted wilt virus (TSWV) resistance and leaf scorch resistance caused by *Leptosphaerulina crassiasca* (Séchet) Jackson and Bell, and high yield. 'Georgia-18RU' provides a medium maturity runner-type peanut cultivar with a prominent main stem, medium green foliage, medium-large runner seed size, and pink seedcoat color.

28 Claims, No Drawings

PEANUT VARIETY 'GEORGIA-18RU'

FIELD

This disclosure provides a new and distinctive peanut variety, 'Georgia-18RU', which is a high-yielding runner-type peanut resistant to tomato spotted wilt caused by Tomato Spotted Wilt Virus (TSWV) and leaf scorch [caused by *Leptosphaerulina crassiasca* (Sechet) Jackson and Bell].

BACKGROUND

The peanut is an annual herbaceous plant of the legume family. Originally cultivated in South America and the eastern slopes of the Andes mountains, peanuts are grown worldwide in the tropic and temperate zones and is a major oilseed crop and rich source of protein.

There are four U.S. peanut market types (runner, virginia, spanish, and valencia). The runner-type, as well as the virginia-type, are classified as (*A. hypogaea* subspecies *hypogaea* var. *hypogaea*), valencia-type (*A. fastigiata* var. *fastigiata*) and spanish-type (*A. hypogaea* subsp. *fastigiata* var. *vulgaris*). Peanuts in the runner-type market class are the most commonly used varieties and are found in diverse products such as peanut butter, salted nuts, and confectionery products. On the other hand, peanut varieties in the virginia market class are largely used as salted nuts and in-shell market. The valencia is largely used in peanut butter, while the spanish type is used in certain niche markets where small round peanuts are needed, such as confectionery products and red skin peanuts.

Peanut is an important and valuable oilseed crop and a rich source of protein. In the United States, peanuts are primarily utilized as whole seeds for human foods such as peanut butter, roasted seeds, and confections. Peanuts are rich in nutrients, providing over 30 essential nutrients and phytonutrients, and are a good source of niacin, folate, fiber, magnesium, vitamin E, manganese and phosphorus. They are also naturally free of trans-fats and sodium, and contain about 25% protein.

Peanut is particularly susceptible to viruses and fungi during growth and storage. Indeed, diseases are major constraints to peanut production worldwide, including spotted wilt caused by the pathogen Tomato Spotted Wilt Virus (TSWV) and leaf scorch caused by *Leptosphaerulina crassiasca* (Sechet) Jackson and Bell. Peanut varieties resistant to such pathogens are needed.

SUMMARY

The present disclosure relates to a new peanut variety, 'Georgia-18RU'. This new variety is a high-yielding, normal-oleic, Tomato spotted wilt virus (TSWV) resistant and leaf scorch [caused by *Leptosphaerulina crassiasca* (Sechet) Jackson and Bell] resistant, medium-large seeded, runner-type peanut (*Arachis hypogaea* L. subsp. *hypogaea* var. *hypogaea*) cultivar developed in Tifton, Ga. 'Georgia-18RU' originated from a cross made between two sister lines of 'Georgia-10T and 'Georgia-09B'. Pedigree selection was practiced within the early-segregating generations. Performance testing began in the $F_{4:6}$ generation with the advanced pure-line selection, 'GA 122540', the experimental designation of 'Georgia-18RU'. During five-years (2013-17) averaged over 34 multilocation tests in Georgia, 'Georgia-18RU' had significantly higher TSMK grade and lowest seed weight compared to 'Georgia-06G. 'Georgia-18RU' is most similar to 'Georgia-06G', and should be another excellent cultivar for a normal-oleic option in the U.S. peanut production area. 'Georgia-18RU' has no genetically modified organisms (GMO) in its ancestry.

A deposit of the new peanut variety 'Georgia-18RU' will be made with the American Type Culture Collection (ATCC), 10801 University Blvd., Manassas, Va., 20110. The date of deposit is Jun. 22, 2021. The deposit is intended to meet all of the requirements of 37 C.F.R. §§ 1.801-1.809. The accession number for those deposited seeds of the new peanut variety 'Georgia-18RU' is ATCC Accession No. PTA-127083. The deposit will be maintained in the depository for a period of 30 years, or 5 years after the last request, or for the effective life of the patent, whichever is longer, and will be replaced if necessary during that period. In one embodiment, the disclosure provides peanut seed deposited as ATCC Accession No. PTA-127083, as well as bulk peanut seed containing such seeds.

The disclosure provides peanut plants having or consisting of the morphological and physiological characteristics of 'Georgia-18RU', such as the characteristics noted in Tables 2-10, for example TSWV resistance, leaf scorch resistance caused by *Leptosphaerulina crassiasca* (Séchet) Jackson and Bell, high percentage of total sound mature kernels (TSMK), small seed weight, high pod yield, small percentage of large fancy pods (e.g., ≥13.49 mm size distribution), high percentage of total meat content, medium maturity, runner growth habit, prominent main stem, medium green foliage, medium-large runner seed size, pink seedcoat (testa) color, or combination thereof. In some examples, a 'Georgia-18RU' plant or progeny thereof has a TSWV resistance of at least 2%, at least 3%, at least 3.4%, at least 4%, at least 4.5%, at least 5%, or at least 5.4%; a leaf scorch resistance rating of no more than 1, no more than 0.5, no more than 0.2, or no more than 0.1; a TSMK of at least 75%, at least 76%, at least 77%, at least 78%, at least 79%, or least 80%; a seed weight of at least 600 seeds per pound, at least 630 seeds per pound, at least 640 seeds per pound, at least 650 seeds per pound, at least 670 seeds per pound, or at least 700 seeds per pound; a yield of at least 4500 pounds/acre (lb/a), at least 4700 lb/a, at least 4800 lb/a, at least 5000 lb/a, at least 5200 lb/a, at least 5500 lb/a, or at least 5800 lb/a; no more than 40% fancy pods (e.g., ≥13.49 mm size distribution), no more than 30% fancy pods, or no more than 25% fancy pods; or combinations thereof. Also provided are seeds of such plants, progeny of such plants, and parts of such plants (such as pollen, ovules and cells). In one example, the disclosure provides peanut plants having the genotype of 'Georgia-18RU'. For example, the disclosure provides plants produced by growing the seed of the new peanut variety 'Georgia-18RU'.

The disclosure provides a tissue culture of regenerable cells of the new peanut variety 'Georgia-18RU', as well as plants regenerated therefrom. Such regenerated peanut plants can include or consist of the physiological and morphological characteristics of a plant grown from the seed of the new peanut variety 'Georgia-18RU'. Exemplary regenerable cells include but are not limited to those from protoplasts or cells, such as those from embryos, meristematic cells, pollen, leaves, roots, root tips, anther, pistil, flower, seed, cotyledon, hypocotyl, shoot, pedicel, petiole, or stem of the new peanut variety 'Georgia-18RU'.

Methods of producing peanut seed from the 'Georgia-18RU' peanut plants are provided. In some examples such methods include crossing 'Georgia-18RU' with itself or a second peanut plant and harvesting a resulting peanut seed. In some examples, the second peanut plant has one or more desirable traits, which is/are introduced into (e.g., via transformation) plants and seeds resulting from such a cross. For example, the second plant can be transgenic, wherein the transgene confers the desirable trait(s). Seeds produced by such methods, including $F_1$ hybrid seeds, as well as peanut plants or parts thereof produced by growing such a seed, are provided. In some examples, the method of crossing includes planting seeds of the new peanut variety 'Georgia-18RU', cultivating peanut plants resulting from the seeds until the plants bear flowers, allowing fertilization of the flowers of the plants; and harvesting seeds produced from the plants.

Methods are provided for producing a plant of peanut variety 'Georgia-18RU' that has one or more added desired traits, as well as plants and seeds generated from such methods. In one example, such a method provides a peanut plant having a single locus conversion of the new peanut variety 'Georgia-18RU', wherein the peanut plant includes or expresses the physiological and morphological characteristics of the new peanut variety 'Georgia-18RU' (such as those shown in Tables 2-10). In some embodiments, the single locus conversion can include a dominant or recessive allele. Such methods can include introducing a transgene that confers one or more desired traits into a plant of the new peanut variety 'Georgia-18RU' (e.g., via transformation). Exemplary desired traits include herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance (such as tolerance to drought, heat, cold, low or high soil pH level, and/or salt); modified phosphorus content, modified antioxidant content, modified essential seed amino acid content, modified fatty acid content, modified carbohydrate content, and modified peanut fiber content, modified oil content, modified protein content, or other improved nutritional qualities.

Methods of introducing a single locus conversion (such as a desired trait) into the new peanut variety 'Georgia-18RU' are provided. In some examples the methods include (a) crossing a plant of variety 'Georgia-18RU' with a second plant having one or more desired traits to produce $F_1$ progeny plants; (b) selecting $F_1$ progeny plants that have the desired trait to produce selected $F_1$ progeny plants; (c) crossing the selected progeny plants with at least a first plant of variety 'Georgia-18RU' to produce backcross progeny plants; (d) selecting backcross progeny plants that have the desired trait and physiological and morphological characteristics of peanut variety 'Georgia-18RU' to produce selected backcross progeny plants; and (e) repeating steps (c) and (d) one or more times in succession to produce selected second or higher backcross progeny plants that include the desired trait and the physiological and morphological characteristics of peanut variety 'Georgia-18RU' when grown in the same environmental conditions. In some embodiments, the single locus confers a desirable trait, such as herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance (such as tolerance to drought, heat, low or high soil pH level, and/or salt), modified phosphorus content, modified antioxidant content; modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, and/or modified pod color. In some examples, the single locus confers the ability to synthesize a protein encoded by a gene located within the single locus.

Methods of producing a peanut plant derived from the new peanut variety 'Georgia-18RU', such as an inbred peanut plant, are provided. In particular examples the method includes (a) preparing a progeny plant derived from the new peanut variety 'Georgia-18RU' by crossing a plant of 'Georgia-18RU' with a peanut plant of a second variety; and (b) crossing the progeny plant with itself or a second plant to produce a progeny plant of a subsequent generation which is derived from a plant of the new peanut variety 'Georgia-18RU'. In some embodiments, the method further includes (c) growing a progeny plant of a subsequent generation from said seed and crossing the progeny plant of a subsequent generation with itself or a second plant; and (d) repeating steps (b) and (c) for at least 2 additional generations (such as at least 3, at least 5, or at least 10 additional generations, such as 2, 3, 4, 5, 6, 7, 8, 9, 10, 11, 12, 13, 14, 15, 16, 17, 18, 19 or 20 additional generations) with sufficient inbreeding to produce an inbred peanut plant derived from the new peanut variety 'Georgia-18RU'. In other examples, the method includes (a) crossing a peanut plant derived from the new peanut variety 'Georgia-18RU' with itself or another peanut plant to yield additional peanut variety 'Georgia-18RU'-derived progeny peanut seed; (b) growing the progeny peanut seed of (a) under plant growth conditions, to yield additional peanut variety 'Georgia-18RU'-derived peanut plants; and (c) repeating the crossing and growing steps of (a) and (b) from 0 to 7 times (such as 0 to 4 or 1 to 5 times, such as 0, 1, 2, 3, 4, 5, 6, or 7 times) to generate further peanut variety 'Georgia-18RU'-derived peanut plants.

Methods are provided for developing a new peanut plant using the new 'Georgia-18RU' variety. For example, the methods can include using 'Georgia-18RU' plants or parts thereof as a source of breeding material in plant breeding techniques, such as recurrent selection, mass selection, bulk selection, backcrossing, pedigree breeding, genetic marker-assisted selection and genetic transformation. In some examples, a plant of the new peanut variety 'Georgia-18RU' is used as the male or female parent.

The disclosure provides a first generation ($F_1$) hybrid peanut seed produced by crossing a plant of the new peanut variety 'Georgia-18RU' to a second peanut plant. In some embodiments, the $F_1$ hybrid peanut plant is grown from the hybrid seed produced by crossing the new peanut variety 'Georgia-18RU' to a second peanut plant. In some examples, the resulting the $F_1$ hybrid peanut plant is treated with glufosinate to identify glufosinate-tolerant progeny. In specific examples, provided is a seed of an $F_1$ hybrid plant produced with the new peanut variety 'Georgia-18RU' as one parent, the second generation ($F_2$) hybrid peanut plant grown from the seed of the $F_1$ hybrid plant, and the seeds of the $F_2$ hybrid plant.

Methods of producing hybrid peanut seeds are also provided. In one example the method includes crossing the new peanut variety 'Georgia-18RU' to a second, distinct peanut plant which is nonisogenic to the new peanut variety 'Georgia-18RU'. In some examples, the method includes cultivating peanut plants grown from seeds of the new peanut variety 'Georgia-18RU' and cultivating peanut plants grown from seeds of a second, distinct peanut plant, until the plants bear flowers. A flower on one of the two plants is cross pollinated with the pollen of the other plant, and the seeds resulting from such a cross are harvested.

The disclosure also provides peanut plants and parts thereof produced by any of the methods disclosed herein. Thus, provided herein are plants of peanut variety 'Georgia-18RU' that further include a single locus conversion, such as one or more desired traits, for example produced by back-crossing or genetic transformation. In some embodiments, the peanut plants produced by the disclosed methods includes at least two, at least three, at least four, at least five, or at least 10 of the traits of the new peanut variety 'Georgia-18RU' as described herein. In some embodiments, the peanut plants produced by the disclosed methods include at least two, at least three, at least four, at least five, or at least 10 of the traits of the new peanut variety 'Georgia-18RU' (see Tables 2-10), such as 2, 3, 4, or all 5 of TSWV resistance, leaf scorch resistance caused by *Leptosphaerulina crassiasca* (Séchet) Jackson and Bell, high percentage of TSMK, small seed weight, high pod yield, small percentage of large fancy pods (e.g., ≥13.49 mm size distribution), and medium-large runner seed size.

Methods of producing a commodity plant product are provided. In some examples the method includes obtaining or supplying a plant of the new peanut variety 'Georgia-18RU', or a part thereof, and producing the commodity plant product therefrom. In some examples the method includes growing and harvesting the plant, or a part thereof. Exemplary commodity plant products include but are not limited to a protein concentrate, a protein isolate, peanut oil, peanut butter, roasted peanuts, salted peanuts, livestock feed, peanut flour, soaps, and/or plastics.

The foregoing and other objects and features of the disclosure will become more apparent from the following detailed description.

DETAILED DESCRIPTION

Description of Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entireties.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Cell. Cell as used herein includes a plant cell, whether isolated, in tissue culture or incorporated in a plant or plant part.

Cotyledon. A type of seed leaf. The cotyledon contains the food storage tissues of the seed.

Cross. Synonymous with hybridize or crossbreed. Includes the mating of genetically different individual plants, such as the mating of two parent plants.

Cross-pollination: Fertilization by the union of two gametes from different plants.

$F_1$ hybrid: The first generation progeny of the cross of two nonisogenic plants.

Flower. Refers all parts of the flower, including but not limited to, stigma, style, ovary, anther, filament, corolla, and calyx.

Gene. Refers to a segment of nucleic acid. A gene can be introduced into a genome of a species, whether from a different species or from the same species, using transformation or various breeding techniques. In some examples, a gene encodes a desirable trait, such as herbicide resistance.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Leaf scorch: A condition in peanut leaflets caused by the fungus *Leptosphaerulina crassiasca*, such as *Leptosphaerulina crassiasca* (Séchet) Jackson and Bell. Scorch symptoms typically start near the tip of the leaflet. Symptoms may or may not start as with a dark circular lesion, surrounded by a halo. If the circular lesion is present, the next stage is development of a wedge-shaped lesion with a bright yellow margin and brown center. The leaf may eventually shrivel, or fall from the plant. The visual score (for example determined using 12× or higher hand lens) is based on the average of the plants in a plot with a score of 0 to 5, with a score of 0=None (0%); 1=slight; 2=slight-moderate; 3=moderate; 4=moderate-severe; and 5=severe (>80%).

Lodging: The visual rating of the uprightness of the plants. The score is based on the average of the plants in a plot with a score of 1 to 5, with a score of 1 indicating all plants are erect, and a score of 5 where over about 80% of the plants in a plot are prostrate.

Maturity date: The evaluation of plants considered as mature when the highest percentage of the pods have reached the mature colors, black, brown, and orange.

Peanut flour. Flour high in protein, often used as a gluten-free solution. Can be generated from peanuts obtained from the disclosed new variety.

Peanut oil. Often used in cooking, it has a mild flavor, high smoke point, and high monounsaturated content. Variations include aromatic roasted peanut oil, refined peanut oil, extra virgin or cold pressed peanut oil, and peanut extract. Can be generated from peanuts obtained from the disclosed new variety.

Plant: Includes reference to an immature or mature whole plant, including a plant from which seed, roots or leaves have been removed. Seed or embryo that will produce the plant is also considered to be the plant.

Plant height. Plant height is taken from the top of the soil to the tip of the plant, and is typically measured in centimeters or inches.

Plant parts. Includes protoplasts, leaves, stems, roots, root tips, anthers, pistils, seed, embryo, pollen, ovules, cotyledon, hypocotyl, flower, shoot, tissue, petiole, cells, pods, meristematic cells and the like. Includes plant cells of a tissue culture from which peanut plants can be regenerated.

Pod. Refers to the fruit of a peanut plant. It consists of the hull or shell (pericarp) and the peanut seeds.

Progeny. Offspring; descendants. Includes an $F_1$ peanut plant produced from the cross of two peanut plants where at least one plant includes peanut cultivar 'Georgia-18RU' and progeny further includes, but is not limited to, subsequent $F_2$, $F_3$ $F_4$, $F_5$, $F_6$, $F_7$, $F_8$, $F_9$, and $F_{10}$ generational crosses with the recurrent parental line.

Regeneration. The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Relative maturity: Refers to the maturity grouping designated by the peanut industry over a given growing area. This figure is generally divided into tenths of a relative maturity group. Within narrow comparisons, the difference of a tenth of a relative maturity group equates very roughly to a day difference in maturity at harvest.

Resistance. The ability of a plant to prevent infection of disease, such as TSWV.

Seed. The part of a flowering plant that typically contains the embryo with its protective coat and stored food and that can develop into a new plant under the proper conditions; fertilized and mature ovule.

Self-pollination: The transfer of pollen from the anther to the stigma of the same plant.

Single locus converted (conversion) plant: Plants developed by backcrossing and/or by genetic transformation, wherein essentially all of the desired morphological and physiological characteristics of a peanut variety are recovered in addition to the characteristics of the single locus transferred into the variety via the backcrossing technique.

Tomato Spotted Wilt Virus (TSWV). A spherical negative-sense RNA virus within the family Bunyaviridae. TSWV, which is commonly transmitted by thrips, causes serious losses in economically important crops and it is one of the most economically devastating plant viruses in the world.

Tissue culture: A composition that includes isolated cells of the same or a different type or a collection of such cells organized into parts of a plant.

Transformation. The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene. A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a peanut plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

New Peanut Resistant to TSWV and Leaf Scorch with High Yield

The present disclosure relates to a new peanut variety, 'Georgia-18RU'. This new variety is TSWV resistant and leaf scorch resistant, and has a high yield. In some examples, 'Georgia-18RU' also has high percentage of TSMK, small seed weight, high pod yield, small percentage of large fancy pods (e.g., ≥13.49 mm size distribution), high percentage of total meat content, medium maturity, runner growth habit, prominent main stem, medium green foliage, medium-large runner seed size, pink seedcoat (testa) color, or combinations thereof. Thus, the new variety is adapted to growth in the United States that commonly grow peanut cultivars and to areas that are known to have or expected to have TSWV and/or *Leptosphaerulina crassiasca* (Sëchet) Jackson and Bell.

In some examples, a 'Georgia-18RU' plant or progeny thereof has a TSWV resistance of at least 2%, at least 3%, at least 3.4%, at least 4%, at least 4.5%, at least 5%, or at least 5.4%; a leaf scorch resistance rating of no more than 1, no more than 0.5, no more than 0.2, or no more than 0.1; a TSMK of at least 75%, at least 76%, at least 77%, at least 78%, at least 79%, or least 80%; a seed weight of at least 600 seeds per pound, at least 630 seeds per pound, at least 640 seeds per pound, at least 650 seeds per pound, at least 670 seeds per pound, or at least 700 seeds per pound; a yield of at least 4500 pounds/acre (lb/a), at least 4700 lb/a, at least 4800 lb/a, at least 5000 lb/a, at least 5200 lb/a, at least 5500 lb/a, or at least 5800 lb/a; no more than 40% fancy pods (e.g., ≥13.49 mm size distribution), no more than 30% fancy pods, or no more than 25% fancy pods; or combinations thereof.

Thus provided herein is a seed of peanut variety 'Georgia-18RU', wherein representative sample seed of the variety will be deposited under (ATCC Accession No. PTA-127083). Also provided are bulk peanut seed containing such seeds. The disclosure provides peanut plants having or consisting of the morphological and physiological characteristics of 'Georgia-18RU'. The disclosure also provides peanut plants having one or more of (such as at least two, at least three, at least four, at least five, at least 6, at least 7, at least 8, at least 9, or at least 10 of) the morphological and physiological characteristics of 'Georgia-18RU' (such as those listed in Tables 2-10). Also provided are seeds of such plants, progeny of such plants, parts of such plants (such as pollen, ovules and cells). In one example, the disclosure provides peanut plants having the genotype of 'Georgia-18RU'. For example, the disclosure provides plants produced by growing the seed of the new peanut variety 'Georgia-18RU'.

The disclosed 'Georgia-18RU' plants, and in some examples progeny thereof, have a pink testa, runner growth habit, higher percentage of total sound mature kernels (TSMK), and smaller seed weight or higher seed count per pound as compared to at least one other peanut, such as 'Georgia-06B'.

The disclosed 'Georgia-18RU' plants and seeds can be used to produce other peanut plants and seeds, for example as part of a breeding program. Choice of breeding or selection methods using to generate new peanut plants and seeds can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location can be effective, whereas for traits with low heritability, selection can be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding can be used to transfer one or a few favorable genes for a highly heritable trait into a desirable variety. This approach has been used for breeding disease-resistant varieties (e.g., see Bowers et al., 1992. *Crop Sci.* 32(1):67-72; Nickell and Bernard, 1992. *Crop Sci.* 32(3):835). Various recurrent selection techniques can be used to improve quantitatively inherited traits controlled by numerous genes.

Promising advanced breeding lines can be thoroughly tested and compared to appropriate standards in environments representative of the commercial target area(s) for generally three or more years. The best or most preferred lines are candidates for new commercial varieties. Those still deficient in a few traits may be used as parents to produce new populations for further selection.

One method of identifying a superior plant is to observe its performance relative to other experimental plants and to one or more widely grown standard varieties. Single observations can be generally inconclusive, while replicated observations provide a better estimate of genetic worth.

Plant breeding can result in new, unique and superior peanut varieties and hybrids from 'Georgia-18RU'. Two or more parental lines can be selected (such as 'Georgia-18RU' as one of the lines), followed by repeated selfing and selection, producing many new genetic combinations. Each year, the germplasm to advance to the next generation is selected. This germplasm is grown under unique and different geographical, climatic and soil conditions, and further selections are then made, during and at the end of the growing season.

In some examples, new peanut varieties developed from 'Georgia-18RU' (such as $F_1$, $F_2$, $F_3$, $F_4$, $F_5$, $F_6$, $F_7$ $F_8$, $F_9$, or $F_{10}$ progeny, or even later progeny) are exposed to TSWV and/or *Leptosphaerulina crassiasca* (Séchet) Jackson and Bell to confirm they are resistant to such diseases.

The development of new peanut varieties from 'Georgia-18RU' involves the development and selection of peanut varieties, the crossing of these varieties and selection of progeny from the superior hybrid crosses. A hybrid seed is produced by manual crosses between selected male-fertile parents or by using male sterility systems. Hybrids can be identified by using certain single locus traits such as pod color, flower color, seed color, or pubescence color, which indicate that the seed is truly a hybrid. Additional data on parental lines as well as the phenotype of the hybrid can influence a decision whether to continue with the specific hybrid cross.

Pedigree breeding and recurrent selection breeding methods can be used to develop varieties from breeding populations. Breeding programs combine desirable traits from two or more varieties or various broad-based sources into breeding pools from which varieties are developed by selfing and selection of desired phenotypes. Pedigree breeding is commonly used for the improvement of self-pollinating crops. Two parents (e.g., wherein one of the parents is 'Georgia-18RU') which possess favorable, complementary traits are crossed to produce an $F_1$. An $F_2$ population is produced by selfing one or several $F_1$'s, such as $F_1$ treated with glufosinate and having tolerance to glufosinate. Selection of the best or most preferred individuals can begin in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (e.g., $F_6$ and $F_7$), the best lines or mixtures of phenotypically similar lines can be tested for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding can be used to transfer genetic loci for simply inherited, highly heritable traits into a desirable homozygous variety which is the recurrent parent (e.g., 'Georgia-18RU'). The source of the trait to be transferred is called the donor or nonrecurrent parent. The resulting plant is expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population are represented by a progeny when generation advance is completed.

In a multiple-seed procedure, one or more pods from each plant in a population are commonly harvested and threshed together to form a bulk. Part of the bulk is used to plant the next generation and part is put in reserve. The procedure has been referred to as modified single-seed descent or the pod-bulk technique. The multiple-seed procedure has been used to save labor at harvest. It is faster to thresh pods with a machine than to remove one seed from each by hand for the single-seed procedure. The multiple-seed procedure also makes it possible to plant the same number of seeds of a population each generation of inbreeding. Sufficient numbers of seeds are harvested to make up for those plants that did not germinate or produce seed.

Descriptions of other breeding methods commonly used for different traits and crops can be found in one of several reference books (e.g., Allard. 1960. Principles of plant breeding. Davis, Calif.: John Wiley & Sons, NY, University of California, pp. 50-98; Simmonds. 1979. Principles of crop improvement. New York: Longman, Inc., pp. 369-399; Sneep and Hendriksen. 1979. "Plant breeding perspectives." Wageningen (ed.), Center for Agricultural Publishing and Documentation; Fehr. 1987. "Principles of variety development." Theory and Technique (Vol. 1). Methods for transformation and regeneration of peanut cells, and specific genes associated with improved peanut traits that may be introduced into 'Georgia-18RU' include those described in Ozias-Akins et al., Plant Science 93:185-194 (1993). In addition, methods for producing novel peanut lines through selection are described in Moore et al., J. Heredity 80(3): 252 (1989); Norden, A. J., Peanuts, Culture and Uses. Am. Peanut Res. And Educ. Soc., Stillwater, Okla. (C. T. Wilson ed. 1973); Norden, A. J. in Hybridization of Crop Plants (H. H. Hadley ed. 1980); Norden et al., Breeding of the cultivated peanut in Peanut Science and Technology, (H. E. Pattee ed. 1992); Norden et al., Florida Agr. Res. 3:16-18 (1984); Knauft et al., Peanut, Peanut Principles of Cultivar Development, 2:346-384 (Walter R. Fehr ed. 1987).

Breeding Peanut Variety 'Georgia-18RU'

Methods for crossing the new peanut variety 'Georgia-18RU' with itself or a second plant are provided, as are the seeds and plants produced by such methods. Such methods can be used for propagation of the new peanut variety 'Georgia-18RU', or progeny thereof, can be used to produce hybrid peanut seeds and the plants grown therefrom. Hybrid peanut plants can be used, for example, in the commercial production of soy products or in breeding programs for the production of novel peanut varieties. A hybrid plant can also be used as a recurrent parent at any given stage in a backcrossing protocol during the production of a single locus conversion (for example introduction of one or more desirable traits) of the new peanut variety 'Georgia-18RU'.

Methods of producing peanut plants and/or seed are provided. Such a method can include crossing the new peanut variety 'Georgia-18RU' with itself or a second peanut plant and harvesting a resulting peanut seed, such as an $F_1$ hybrid seed. The resulting plant can be grown, resulting in a peanut plant or part thereof.

In one example methods of producing an inbred peanut plant derived from peanut variety 'Georgia-18RU' are provided. In one example such methods include (a) preparing a progeny plant derived from peanut variety 'Georgia-18RU' by crossing a plant of the peanut variety 'Georgia-18RU' with a peanut plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred peanut plant derived from the peanut variety 'Georgia-18RU'.

The second plant crossed with the new peanut variety 'Georgia-18RU' for the purpose of developing novel peanut varieties, is typically a plant which either themselves exhibit one or more desirable characteristics or which exhibit one or more desired characteristic(s) when in hybrid combination. In one example, the second peanut plant is transgenic. Exemplary desired characteristics include, but are not limited to, one or more of: increased seed yield, lodging resistance, emergence, increased seedling vigor, modified maturity date, desired plant height, high oil content, high protein content, herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance; modified phosphorus content, modified antioxidant content; modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, and modified pod color.

When the new peanut variety 'Georgia-18RU' is crossed with another different variety, first generation ($F_1$) peanut progeny are produced. The hybrid progeny are produced regardless of characteristics of the two varieties produced. As such, an $F_1$ hybrid peanut plant can be produced by crossing 'Georgia-18RU' with any second peanut plant. The second peanut plant can be genetically homogeneous (e.g., inbred) or can itself be a hybrid. Therefore the disclosure provides any $F_1$ hybrid peanut plant produced by crossing the new peanut variety 'Georgia-18RU' with a second peanut plant (such as a transgenic plant having one or more genes that confer to the plant one or more desired characteristics).

Peanut plants can be crossed by either natural or mechanical techniques. Natural pollination occurs in peanut plants either by self-pollination or natural cross pollination, which typically is aided by pollinating organisms. In either natural or artificial crosses, flowering time can be a consideration.

The peanut plant grows best in light, sandy soil and typically requires four to five months of warm weather and an annual rainfall of 20 to 39 inches, or the equivalent in irrigation water. The pea-like yellow flowers form in axillary clusters and only bloom for a short time. Following self-pollination, the stalk at the base of the ovary, called the pedicel, elongates rapidly and turns downward to bury the fruits one to several inches below the ground surface. The peanut pods complete their development 120 to 150 days after planting. During harvest, the entire plant including the roots is removed from the soil.

In some examples, the crossing of two peanut plants is accomplished using artificial hybridization. In artificial hybridization, the flower used as a female in a cross is manually cross pollinated prior to maturation of pollen from the flower, thereby preventing self-fertilization, or alternatively, the male parts of the flower are emasculated. Exemplary methods for emasculating the male parts of a peanut flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed, for example with forceps. Immature buds, such as those hidden under the stipules at the leaf axil, are removed. The calyx is removed, for example by grasping a sepal with the forceps, pulling it down and around the flower, and repeating the procedure until the five sepals are removed. The exposed corolla is removed, for example by grasping it just above the calyx scar, then lifting and wiggling the forceps simultaneously. The ring of anthers is visible after the corolla is removed, unless the anthers were removed with the petals. Cross-pollination can then be performed using, for example, petri dishes or envelopes in which male flowers have been collected. Desiccators containing calcium chloride crystals are used in some environments to dry male flowers to obtain adequate pollen shed.

Emasculation is not necessary to prevent self-pollination (Walker et al. 1979. *Crop Sci.* 19:285-286). When emasculation is not used, the anthers near the stigma can be removed to make the stigma visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Peanut Plants Having One or More Desired Heritable Traits

The disclosure provides plants of the new peanut variety 'Georgia-18RU' modified to include one or more desired heritable traits. In some examples, such plants can be developed using backcrossing or genetic engineering (for example by introducing one or more transgenes into the 'Georgia-18RU' variety, wherein the transgenes encode one or more desired traits), wherein essentially all of the desired morphological and physiological characteristics of the 'Georgia-18RU' variety are recovered, such as TSWV resistance and leaf scorch resistance *Leptosphaerulina crassiasca* (Séchet) Jackson and Bell, and in some examples one or more of high percentage of total sound mature kernels (TSMK), small seed weight, high pod yield, small percentage of large fancy pods (e.g., ≥13.49 mm size distribution), high percentage of total meat content, medium maturity, runner growth habit, prominent main stem, medium green foliage, medium-large runner seed size, and pink seedcoat (testa) color, in addition to a genetic locus transferred into the plant via the backcrossing technique. Plants developed using such methods can be referred to as a single locus converted plant.

In one example, the method of introducing one or more desired traits into peanut variety 'Georgia-18RU' includes (a) crossing a plant of variety 'Georgia-18RU' with a second plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of variety 'Georgia-18RU' to produce backcross progeny plants; (d) selecting backcross progeny plants that have the one or more desired traits and physiological and morphological characteristics of peanut variety 'Georgia-18RU' to produce selected backcross progeny plants; and (e) repeating steps (c) and (d) one or more times in succession to produce selected second or higher backcross progeny plants that have the one or more desired traits and the physiological and morphological characteristics of peanut variety 'Georgia-18RU' when grown in the same environmental conditions.

Backcrossing methods can be used to improve or introduce a characteristic into the new peanut variety 'Georgia-18RU' (for example using the methods provided in U.S. Pat. No. 6,140,556). The parental peanut plant which contributes the locus for the desired characteristic is termed the "nonrecurrent" or "donor" parent. This terminology refers to the fact that the nonrecurrent parent is used one time in the backcross protocol and therefore does not recur. The parental peanut plant to which the locus or loci from the nonrecurrent parent are transferred is known as the recurrent parent as it is used for several rounds in the backcrossing protocol (Poehlman and Sleper. 1995. "Breeding Field Crops" Ames, Iowa: Iowa State University Press; Fehr. 1987. "Principles of variety development." In Theory and Technique (Vol. 1) and Crop Species peanut (Vol. 2). New York: Macmillan Publishing Company, pp. 360-376; Sprague and Dudley, eds. 1988. Corn and Improvement, 3rd edition). In a typical backcross protocol, the original variety of interest (recurrent parent, e.g., 'Georgia-18RU') is crossed to a second variety (nonrecurrent parent) that carries the single locus of interest (such as a desirable trait) to be transferred. The resulting progeny from this cross are then crossed again to the recurrent parent and the process is repeated until a peanut plant is obtained wherein essentially all of the desired morphological and physiological characteristics of the recurrent parent (e.g., 'Georgia-18RU') are recovered (such as TSWV resistance, leaf scorch resistance caused by *Leptosphaerulina crassiasca* (Séchet) Jackson and Bell, high percentage of total sound mature kernels (TSMK), small seed weight, high pod yield, small percentage of large fancy pods (e.g., ≥13.49 mm size distribution), high percentage of total meat content, medium maturity, runner growth habit, prominent main stem, medium green foliage, medium-large runner seed size, pink seedcoat (testa) color, or combination thereof) in the converted plant, in addition to the single transferred locus from the nonrecurrent parent.

The goal of a backcross protocol is to alter or substitute a single trait or characteristic in the original variety, such as 'Georgia-18RU'. To accomplish this, a single locus of the recurrent variety is modified or substituted with the desired locus from the nonrecurrent parent, while retaining essentially all of the rest of the desired genetic traits, and therefore the desired physiological and morphological constitution of the original variety. The choice of the particular nonrecurrent parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield or resistance to a pest. As in this example, lines with the phenotype of the recurrent parent can be composited without the usual replicated tests for traits such as yield, protein or oil percentage in the individual lines.

Peanut varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease, insect resistance, restoration of male fertility, enhanced nutritional quality, modified phosphorus content, modified antioxidant content; modified essential seed amino acid content, modified fatty acid content, modified carbohydrate content, modified peanut fiber content, yield stability, and yield enhancement, low pod-splitting, modified seed yield, modified oil percent, modified protein percent, modified fancy pod percent, modified pod size, modified pod shape, and modified pod color. These comprise genes generally inherited through the nucleus. Thus plants of peanut variety 'Georgia-18RU' that include a single locus conversion (such as one that confers a desired trait) are provided herein.

Direct selection can be applied where the single locus acts as a dominant trait. An example of a dominant trait is the herbicide resistance trait (such as glufosinate tolerance). For the selection process, the progeny of the initial cross are sprayed with an herbicide (such as glufosinate) prior to the backcrossing. The spraying eliminates any plants which do not have the desired herbicide tolerance characteristic; only those plants which have the herbicide resistance gene are used in the subsequent backcross. This process is then repeated for all additional backcross generations.

Selection of peanut plants for breeding may not be dependent on the phenotype of a plant and instead can be based on genetic investigations. For example, a suitable genetic marker can be used which is closely genetically linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to the breeding of peanut are known. Such methods can be useful in the case of recessive traits and variable phenotypes, or where conventional assays are more expensive, time consuming or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858), and Single Nucleotide Polymorphisms (SNPs).

Qualitative characters can be useful as phenotype-based genetic markers in peanuts; however, some or many may not differ among varieties commonly used as parents. Widely used genetic markers include flower color, seed color, and pod color. Differences in maturity, height, TSMK percentage, fancy pod percentage, seed size, seed weight, and pest resistance between parents can also be used to verify hybrid plants.

Useful or desirable traits can be introduced by backcrossing, as well as directly into a plant by genetic transformation methods. Genetic transformation can therefore be used to insert a selected transgene into the 'Georgia-18RU' variety or can, alternatively, be used for the preparation of transgenes which can be introduced by backcrossing. Thus, the disclosure provides methods of producing a plant of peanut variety 'Georgia-18RU' that includes one or more added desired traits, for example that include introducing a transgene(s) conferring the one or more desired traits into a plant of peanut variety 'Georgia-18RU' (for example by transformation with a transgene that confers upon the peanut plant the desired trait), thereby producing a plant of peanut variety 'Georgia-18RU' that includes the one or more added desired traits.

Methods for the transformation of many economically important plants, including peanuts, are known. Methods for introducing a desired nucleic acid molecule (e.g., transgene), such as DNA, RNA, or inhibitory RNAs, are known, and the disclosure is not limited to particular methods. Exemplary techniques which can be employed for the genetic transformation of peanut include, but are not limited to, electroporation, microprojectile bombardment, *Agrobacterium*-mediated transformation direct DNA uptake by protoplasts, sonication of target cells, liposome and spheroplast fusion, CaCl2 precipitation, polyvinyl alcohol, or poly-L-ornithine.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner.

Protoplasts can also be employed for electroporation transformation of plants (Bates. 1994. *Mol. Biotechnol.* 2(2):135-145; Lazzeri. 1995. *Methods Mol. Biol.* 49:95-106). For example, the generation of transgenic peanut plants by electroporation of cotyledon-derived protoplasts and whole cells and tissues has been described (Donn et al., In Abstracts of VIIth International Congress on Plant Cell and Tissue Culture IAPTC, A2-38, p. 53 (1990); D'Halluin et al., Plant Cell, 4:1495-1505 (1992); and Spencer et al., Plant Mol. Biol., 24:51-61 (1994)).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target peanut cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large. Microprojectile bombardment methods can be used to transform peanuts, as described, for example, in U.S. Pat. No. 5,322,783.

*Agrobacterium*-mediated transfer can be used to introduce gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is known (e.g., Fraley et al. 1985. *Bio. Tech.* 3(7):629-635; U.S. Pat. No. 5,563,055), and its use for peanut transformation has been described (Chee and Slightom. 1995. *Methods Mol. Biol.* 44:101-119; U.S. Pat. No. 5,569,834). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189): 454-457). The ability to regenerate peanut plants from protoplasts makes these techniques applicable to peanut.

In one example, such methods can also be used to introduce transgenes for the production of proteins in transgenic peanuts. The resulting produced protein can be harvested from the transgenic peanut. The transgene can be harvested from the transgenic plants that are originated or are descended from the new peanut variety 'Georgia-18RU', a seed of 'Georgia-18RU' or a hybrid progeny of 'Georgia-18RU'.

Numerous different genes are known and can be introduced into a peanut plant 'Georgia-18RU' or progeny thereof. Non-limiting examples of particular genes and corresponding phenotypes that can be chosen for introduction into a peanut plant are provided herein.

Herbicide Resistance

Numerous herbicide resistance genes are known and can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to an herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458).

Resistance genes for glyphosate (e.g., resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes), pyridinoxy or phenoxy proprionic acids, and cyclohexanediones (ACCase inhibitor-encoding genes), can be used (e.g., see U.S. Pat. Nos. 4,940,835; 5,627,061; 6,566,587, 6,338,961, 6,248, 876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, 5,491,288, 5,776,760, 5,463,175, 7,462,481; and International Publications EP1173580, WO 01/66704, EP1173581, and EP1173582). Examples of specific EPSPS transformation events conferring glyphosate resistance are described, for example, in U.S. Pat. No. 6,040,497.

DNA molecules encoding a mutant aroA gene are known (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of transgenic plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Genes conferring resistance to an herbicide that inhibits photosynthesis are also known, such as, a triazine (psbA and gs+ genes) and a benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseuodmonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

Acetohydroxy acid synthase, which has been found to make plants that express this enzyme resistant to multiple types of herbicides, has been introduced into a variety of plants. See, Hattori et al., Mol. Gen. Genet., 246:419 (1995). Other genes that confer tolerance to herbicides include a gene encoding a chimeric protein of rat cytochrome P4507A1 and yeast NADPH-cytochrome P450 oxidoreductase (Shiota et al., Plant Physiol., 106:17 (1994)); genes for glutathione reductase and superoxide dismutase (Aono, et al., Plant Cell Physiol., 36:1687 (1995)); and genes for various phosphotransferases (Datta, et al., Plant Mol. Biol., 20:619 (1992)).

Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes can be introduced into the disclosed 'Georgia-18RU' through a variety of means including but not limited to transformation and crossing.

Disease and Insect Resistance

Plant defenses are often activated by specific interaction between the product of a disease resistance gene (R) in the plant and the product of a corresponding avirulence (Avr) gene in the pathogen. A plant, such as 'Georgia-18RU' or progeny thereof, can be transformed with cloned resistance gene to engineer plants that are resistant to specific pathogen strains. See, for example Jones et al. (1994. *Science* 266:789) (tomato Cf-9 gene for resistance to *Cladosporium flavum*); Martin et al. (1993. *Science* 262(5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclose transgenic plants expressing a barley ribosome-inactivating gene have an increased resistance to fungal disease.

One example of an insect resistance gene includes a *Bacillus thuringiensis* (Bt) protein, a derivative thereof or a synthetic polypeptide modeled thereon (e.g., see Geiser et al., 1986. *Gene* 48:109, discloses a Bt Aendotoxin gene). Moreover, DNA molecules encoding Δ-endotoxin genes can be obtained from ATCC (Manassas, Va.), for example under ATCC Accession Nos. 40098, 67136, 31995 and 31998. Another example is a lectin. See, for example, Van Damme et al. (1994. *Plant Mol Biol* 24(5):825-830), which discloses several *Clivia miniata* mannose-binding lectin genes. A vitamin-binding protein can also be used, such as avidin. See WO 1994/000992, which teaches the use of avidin and avidin homologues as larvicides against insect pests.

In one example the insect resistance gene is an enzyme inhibitor, for example, a protease, proteinase inhibitor, or an α-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. *Nature* 344:458-461; discloses juvenile hormone esterase, an inactivator of juvenile hormone).

Still other examples include an insect-specific antibody or an immunotoxin derived therefrom and a developmental-arrestive protein. See Taylor et al. (1994. Seventh Intl. Symposium on Molecular Plant-Microbe Interactions (Edinburgh Scotland), Abstract #497), who described enzymatic inactivation in transgenic tobacco via production of single-chain antibody fragments.

An enzyme inhibitor, for example, a protease or proteinase inhibitor or an amylase inhibitor can be used. See, for example, Abe et al., J. Biol. Chem., 262:16793 (1987) (nucleotide sequence of rice cysteine proteinase inhibitor); Huub et al., Plant Molec. Biol., 21:985 (1993) (nucleotide sequence of cDNA encoding tobacco proteinase inhibitor I); Sumitani et al., Biosci. Biotech. Biochem., 57:1243 (1993) (nucleotide sequence of *Streptomyces nitrosporeus* .alpha.-amylase inhibitor); and U.S. Pat. No. 5,494,813.

An insect-specific hormone or pheromone, such as an ecdysteroid or juvenile hormone, a variant thereof, a mimetic based thereon, or an antagonist or agonist thereof. See, for example, the disclosure by Hammock et al., Nature, 344:458 (1990), of baculovirus expression of cloned juvenile hormone esterase, an inactivator of juvenile hormone.

An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor); Pratt, et al., Biochem. Biophys. Res. Comm., 163:1243 (1989) (an allostatin is identified in Diploptera puntata); Chattopadhyay, et al., Critical Reviews in Microbiology, 30(1):33-54 (2004); Zjawiony, J Nat Prod, 67(2):300-310 (2004); Carlini & Grossi-de-Sa, Toxicon, 40(11):1515-1539 (2002); Ussuf, et al., Curr Sci., 80(7): 847-853 (2001); Vasconcelos & Oliveira, Toxicon, 44(4): 385-403 (2004). See also, U.S. Pat. No. 5,266,317 to Tomalski, et al., which discloses genes encoding insect-specific, paralytic neurotoxins.

An insect-specific venom produced in nature by a snake, a wasp, etc. For example, see, Pang, et al., Gene, 116:165 (1992), for disclosure of heterologous expression in plants of a gene coding for a scorpion insectotoxic peptide.

An enzyme responsible for a hyperaccumulation of a monoterpene, a sesquiterpene, a steroid, hydroxamic acid, a phenylpropanoid derivative, or another non-protein molecule with insecticidal activity.

An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197, which discloses the nucleotide sequence of a callase gene. DNA molecules which contain chitinase-encoding sequences can be obtained, for example, from the ATCC under Accession Nos. 39637 and 67152. See also, Kramer, et al., Insect Biochem. Molec. Biol., 23:691 (1993), who teach the nucleotide sequence of a cDNA encoding tobacco hornworm chitinase, and Kawalleck, et al., Plant Molec. Biol., 21:673 (1993), who provide the nucleotide sequence of the parsley ubi4-2 polyubiquitin gene, U.S. Pat. Nos. 7,145,060, 7,087,810, and 6,563,020.

A molecule that stimulates signal transduction. For example, see the disclosure by Botella, et al., Plant Molec. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

A membrane permease, a channel former or a channel blocker. For example, see the disclosure of Jaynes, et al., Plant Sci, 89:43 (1993), of heterologous expression of a cecropin-beta lytic peptide analog to render transgenic tobacco plants resistant to *Pseudomonas solanacearum*.

A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., Ann. Rev. Phytopathol., 28:451 (1990). Coat protein-mediated resistance has been conferred upon transformed plants against alfalfa mosaic virus, cucumber mosaic virus, and tobacco mosaic virus.

An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Intl Symposium on Molecular Plant-Microbe Interactions (Edinburgh, Scotland 1994) (enzymatic inactivation in transgenic tobacco via production of single-chain antibody fragments).

A virus-specific antibody. See, for example, Tavladoraki et al., Nature, 366:469 (1993), who show that transgenic plants expressing recombinant antibody genes are protected from virus attack.

A developmental-arrestive protein produced in nature by a pathogen or a parasite. Thus, fungal endo-.alpha.-1,4-D-polygalacturonases facilitate fungal colonization and plant nutrient release by solubilizing plant cell wall homo-.alpha.-1,4-D-galacturonase. See, Lamb, et al., Bio/Technology, 10:1436 (1992). The cloning and characterization of a gene which encodes a bean endopolygalacturonase-inhibiting protein is described by Toubart, et al., Plant J., 2:367 (1992).

A developmental-arrestive protein produced in nature by a plant. For example, Logemann, et al., Bio/Technology, 10:305 (1992), have shown that transgenic plants expressing the barley ribosome-inactivating gene have an increased resistance to fungal disease.

Genes involved in the Systemic Acquired Resistance (SAR) Response and/or the pathogenesis-related genes. Briggs, S., Current Biology, 5(2) (1995); Pieterse & Van Loon, Curr. Opin. Plant Bio., 7(4):456-64 (2004); and Somssich, Cell, 113(7):815-6 (2003).

Antifungal genes. See, Cornelissen and Melchers, Plant Physiol., 101:709-712 (1993); Parijs, et al., Planta, 183:258-264 (1991); and Bushnell, et al., Can. J. of Plant Path., 20(2):137-149 (1998). See also, U.S. Pat. No. 6,875,907.

Detoxification genes, such as for fumonisin, beauvericin, moniliformin, and zearalenone and their structurally-related derivatives. See, for example, U.S. Pat. No. 5,792,931.

Cystatin and cysteine proteinase inhibitors. See, U.S. Pat. No. 7,205,453.

Defensin genes. See, WO 03/000863 and U.S. Pat. No. 6,911,577.

Genes conferring resistance to nematodes, such as root knot nematode and root lesion nematode. See, e.g., WO 96/30517, WO 93/19181, and WO 03/033651; Urwin et al., Planta, 204:472-479 (1998); Williamson, Curr Opin Plant Bio., 2(4):327-31 (1999).

Genes that confer resistance to Phytophthora Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7, and other Rps genes.

Genes that confer resistance to Brown Stem Rot, such as described in U.S. Pat. No. 5,689,035 and incorporated by reference for this purpose.

Any of the above-listed disease or pest resistance genes can be introduced into 'Georgia-18RU' through a variety of means including, but not limited to, transformation and crossing.

Male Sterility

Genetic male sterility can increase the efficiency with which hybrids are made, in that it can eliminate the need to physically emasculate the peanut plant used as a female in a given cross (Brim and Stuber. 1973. *Crop Sci.* 13:528-530). Herbicide-inducible male sterility systems are known (e.g., U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the peanut plant is utilized. However, in many cases, the seeds are considered to be a valuable portion of the crop, thus, it is desirable to restore the fertility of the hybrids in these crops. Therefore, the disclosure provides plants of the new peanut variety 'Georgia-18RU' comprising a genetic locus capable of restoring male fertility in an otherwise male-sterile plant. Examples of male-sterility genes and corresponding restorers which can be employed are known (see, e.g., U.S. Pat. Nos. 5,530,191 and 5,684,242).

There are several methods of conferring genetic male sterility available, such as multiple mutant genes at separate locations within the genome that confer male sterility, as disclosed in U.S. Pat. Nos. 4,654,465 and 4,727,219 and chromosomal translocations as described in U.S. Pat. Nos. 3,861,709 and 3,710,511. In addition to these methods, U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

Introduction of a deacetylase gene under the control of a tapetum-specific promoter and with the application of the chemical N-Ac-PPT. See WO 01/29237.

Introduction of various stamen-specific promoters. See WO 92/13956 and WO 92/13957.

Introduction of the barnase and the barstar genes. See, Paul et al., Plant Mol. Biol., 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640.

Any of the above-listed male sterility genes can be introduced into 'Georgia-18RU' through a variety of means including, but not limited to, transformation and crossing.

Exemplary Genes that Confer a Value-Added Trait

Genes conferring modified fatty acid metabolism can be introduced into 'Georgia-18RU' and its progeny, such as antisense stearoyl acyl carrier protein (ACP) desaturase genes (EC 1.14.99.6) (e.g., Knutzon et al. 1992. *PNAS* 89:2624-2628). Fatty acid desaturases can be introduced into 'Georgia-18RU' and its progeny, such as *Saccharomyces cerevisiae* OLE1 gene encoding 49-fatty acid desaturase, an enzyme which forms the monounsaturated palmitoleic (16:1) and oleic (18:1) fatty acids from palmitoyl (16:0) or stearoyl (18:0) CoA (McDonough et al., 1992. *J Biol Chem* 267(9):5931-5936); a gene encoding a stearoyl-acyl carrier protein Δ-9 desaturase from castor (Fox et al. 1993. *PNAS* 90(6):2486-2490); Δ6- and Δ12-desaturases from the cyanobacteria *Synechocystis* responsible for the conversion of linoleic acid (18:2) to gamma-linolenic acid (18:3 gamma) (Reddy et al., 1993. *Plant Mol Biol* 22(2):293-300); a gene from *Arabidopsis thaliana* that encodes an omega-3 desaturase (Arondel et al. 1992. *Science* 258:1353-5); plant Δ9-desaturases (WIPO Publication No. WO 1991/013972) and peanut and *Brassica* 415 desaturases (European Patent Application Publ. No. EP 0616644).

Phytate metabolism can also be modified by introduction of a phytase-encoding gene to enhance breakdown of phytate, adding more free phosphate to the transformed plant. For example, see Van Hartingsveldt et al. (1993. *Gene* 127:87-94), for an *Aspergillus niger* phytase gene. In peanut, this, for example, could be accomplished by cloning and then reintroducing DNA associated with the single allele which is responsible for peanut mutants characterized by low levels of phytic acid. See Raboy et al. (2000, *Plant Physiol.* 124(1):355-68).

A number of genes can be used to alter carbohydrate metabolism. For example, plants can be transformed with a gene coding for an enzyme that alters the branching pattern of starch or a gene altering thioredoxin, such as NTR and/or TRX (see, U.S. Pat. No. 6,531,648), and/or a gamma zein knock out or mutant, such as cs27 or TUSC27 or en27 (see, U.S. Pat. No. 6,858,778, and U.S. Publ. Nos. 2005/0160488 and 2005/0204418). See, Shiroza et al. (1988. *J Bacteriol* 170(2):810-816) (*Streptococcus* fructosyltransferase gene), Steinmetz et al. (1985. *Mol Gen Genet.* 200:220-228) (*Bacillus subtilis* levansucrase gene), Pen et al. (1992. *BioTechnology* 10:292) (*Bacillus* lichenifonnis α-amylase), Elliot et al. (1993. *Plant Mol. Biol* 21:515) (tomato invertase genes), Sergaard et al. (1993. *J. Biol. Chem.* 268:22480) (site-directed mutagenesis of barley α-amylase gene), and Fisher et al. (1993. *Plant Physiol* 102:1045) (maize endosperm starch branching enzyme II), WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways. The Z10 gene encoding a 10 kD zein storage protein from maize can also be used to alter the quantities of 10 kD zein in the cells relative to other components (Kirihara et al., 1988. *Mol Gen Genet.* 211:477-484).

Elevated oleic acid via FAD-2 gene modification and/or decreased linolenic acid via FAD-3 gene modification. See, U.S. Pat. Nos. 6,063,947, 6,323,392, and WO 93/11245. Although as many as 12 fatty acids have been reported in peanuts, only 3 are present in amounts exceeding 5%: palmitic, oleic and linoleic (Ahmed et al., in Peanut Science and Technology (1982 H. E. Pattec, et al., ed)). These three fatty acids comprise about 90% of the fatty acid composition of the oil, with oleic and linoleic comprising about 80%. The remainder of the fatty acids comprise about 10%, each ranging in concentration from 0.02% to 2.59%. The American Heart Association and the American Heart Foundation have recommended diet modifications to achieve lower serum cholesterol levels in the population. These diet modifications include reducing consumption of saturated fatty acids and thereby increasing the polyunsaturated to saturated (P/S) ratio in the diet (Technical Committee, Food Fats and Oils, 5.sup.th ed. (1992)). Edible peanut oils with a higher percentage of unsaturated fatty acids can be used for these cardio-vascular health reasons (Mattson et al., J Lipid Research 26:194-202 (1985)).

Altering conjugated linolenic or linoleic acid content, such as in WO 01/12800. Altering LEC1, AGP, Dek1, Superal1, mi1ps, and various Ipa genes, such as Ipa1, Ipa3, hpt, or hggt. See, for example, WO 02/42424, WO 98/22604, WO 03/011015, WO 02/057439, WO 03/011015, U.S. Pat. Nos. 6,423,886, 6,197,561, 6,825,397, 7,157,621, U.S. Publ. No. 2003/0079247, and Rivera-Madrid et al., Proc. Natl. Acad. Sci., 92:5620-5624 (1995).

Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

Altered essential seed amino acids. See, for example, U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); U.S. Pat. No. 5,850,016 (alteration of amino acid compositions in seeds); U.S. Pat. No. 5,885,802 (high methionine); U.S. Pat. No. 5,885,801 (high threonine); U.S. Pat. No. 6,664,445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 7,098,381 (UDPGdH); U.S. Pat. No. 6,194,638 (RGP); U.S. Pat. Nos. 6,399,859, 6,930,225, 7,179,955, and 6,803,498; U.S. Publ. No. 2004/0068767; WO 99/40209 (alteration of amino acid compositions in seeds); WO 99/29882 (methods for altering amino acid content of proteins); WO 98/20133 (proteins with enhanced levels of essential amino acids); WO 98/56935 (plant amino acid biosynthetic enzymes); WO 98/45458 (engineered seed protein having higher percentage of essential amino acids); WO 98/42831 (increased lysine); WO 96/01905 (increased threonine); WO 95/15392 (increased lysine); WO 01/79516; and WO 00/09706 (Ces A: cellulose synthase).

Any of the above-listed value-added trait genes can be introduced into 'Georgia-18RU' through a variety of means including, but not limited to, transformation and crossing.

Genes that Create a Site for Site Specific DNA Integration

This includes the introduction of FRT sites that may be used in the FLP/FRT system and/or Lox sites that may be used in the Cre/Loxp system. See, for example, Lyznik, et al., Site-Specific Recombination for Genetic Engineering in Plants, Plant Cell Rep, 21:925-932 (2003) and WO 99/25821, which are hereby incorporated by reference. Other systems that may be used include the Gin recombinase of phage Mu (Maeser, et al. (1991); Vicki Chandler, the Maize Handbook, Ch. 118 (Springer-Verlag 1994)); the Pin recombinase of E. coli (Enomoto, et al. (1983)); and the R/RS system of the pSR1 plasmid (Araki, et al. (1992)).

Any of the above-listed sites can be introduced into 'Georgia-18RU' through a variety of means including, but not limited to, transformation and crossing.

Genes that Affect Abiotic Stress Resistance

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723, and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FR1), WO 97/29123, WO 99/09174 (D8 and Rht), WO 2004/076638, and WO 004/031349 (transcription factors).

Any of the above-listed sites can be introduced into 'Georgia-18RU' through a variety of means including, but not limited to, transformation and crossing.

Tissue Cultures and In Vitro Regeneration of Peanut Plants

Tissue cultures of the new peanut variety 'Georgia-18RU' are provided. Further reproduction of the 'Georgia-18RU' and its progeny can occur by tissue culture and regeneration. Tissue culture of various tissues of peanuts and regeneration of plants there from is known. For example, see Komatsuda et al., Crop Sci., 31:333-337 (1991); Stephens et al., Theor. Appl. Genet., 82:633-635 (1991); Komatsuda, et al., Plant Cell, Tissue and Organ Culture, 28:103-113 (1992); Dhir et al., Plant Cell Reports, 11:285-289 (1992); Pandey et al., Japan J. Breed., 42:1-5 (1992); and Shetty et al., Plant Science, 81:245-251 (1992); as well as U.S. Pat. Nos. 5,024,944, and 5,008,200, issued. Thus, provided are cells, which upon growth and differentiation produce peanut plants having the physiological and morphological characteristics of peanut cultivar 'Georgia-18RU'.

A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, pod, petiole, stein, ovule, cotyledon, hypocotyl, shoot, stem, and the like. In a particular example, the tissue culture includes embryos, protoplasts, meristematic cells, pollen, leaves or anthers of the new peanut variety 'Georgia-18RU'. Also provided are peanut plants regenerated from such tissue cultures, wherein the regenerated peanut plant expresses the physiological and morphological characteristics of the peanut variety 'Georgia-18RU'.

Exemplary methods for preparing and maintaining plant tissue culture are described in. U.S. Pat. Nos. 5,959,185, 5,973,234, and 5,977,445.

Example 1

Breeding History of 'Georgia-18RU'

'Georgia-18RU' is a new high-yielding, tomato spotted wilt virus (TSWV) resistant and leaf scorch resistant, runner-type peanut (*Arachis hypogaea* L. subsp. *hypogaea* var. *hypogaea*) cultivar. It was developed at the University of Georgia, Coastal Plain Experiment Station, in Tifton, Ga.

Details on the breeding history are found in Table 1. 'Georgia-18RU' originated from a cross made in 2007 between two breeding lines, 'GA 052530' x 'GA 032913', (sister lines of 'Georgia-10T' and 'Georgia-09B', respectively). 'Georgia-10T' is a normal-oleic, TSWV-resistant, runner-type peanut cultivar (PVP Cert No. 201100127) that was selected from a cross between 'Georgia-02C' and 'Georgia-01R'. 'Georgia-09B' is a high-oleic, TSWV-resistant, runner market type peanut cultivar (PVP Cert. No. 201000075) that was selected from the first backcross ($BC_1$) between 'Georgia Green' and a high-oleic $F_{2:3}$ Georgia selection from a cross between 'Georgia Green' x 'GA 942004'. Pedigree selection method was practiced within the $F_2$, $F_3$, and $F_4$ segregating populations, and performance testing begun in the $F_{4:6}$ generation with the advanced pure breeding line, 'GA 122540'. For five years (2013-2017), field observation and data indicate that the varietal characteristics of 'Georgia-18RU' are very uniform and stable.

TABLE 1

PEDIGREE SELECTION METHOD

| | |
|---|---|
| 2007 | 'GA 052530' x 'GA 032913' |
| 2008 | $F_1$ Increase |
| 2009-2011 | $F_2$-$F_4$ Individual Resistant Plant Selections* |
| 2012 | $F_5$ Progeny Row Increase |
| 2013-2017 | $F_6$-$F_{10}$ Multilocation Yield Trials |
| 2018 | $F_{11}$ Released as 'Georgia-18RU' |

*Individual plant selections were based upon pod shape, seed size, testa color, growth habit, maturity, yield and grade characteristics. Because tomato spotted wilt virus (TSWV) and leaf scorch were naturally occurring during these early segregation generations, individual plants were also selected for combined TSWV and leaf scorch resistance.

Georgia-18RU was developed using the pedigree selection method for peanut breeding (Knauft et al., 1987. Peanut. Pp. 346-384. In W. R. Fehr (ed.). Principles of Cultivar Development. Vol. 2. Crop Species. Macmillan Publishing Co. New York.). $F_1$ seed were space-planted approximately 122 cm apart in one-row plots, 6.1 m longx1.8 m wide in 2008. $F_2$ seed were space-planted in 2009 approximately 30.5-cm apart in two-row plots, 61.0 m longx1.8 m wide. Individual plant selections were made based upon pod shape, seed size, testa color, growth habit, maturity, pod yield, and grade characteristics. Because TSWV and leaf scorch occurred naturally during these early-segregating generations ($F_2$-$F_4$), individual plants were selected for combined TSWV and leaf scorch resistance.

In 2010, $F_3$ plants were space-planted approximately 30.5-cm apart in two-row plots, 36.6 m longx1.8 m wide. Individual plant selections were made based upon the same selection criteria as in the $F_2$ population.

During 2011, $F_4$ were likewise space-planted approximately 30.5-cm apart in two-row plots, 30.5 m longx1.8 m wide. Individual plant selections were made based upon the same $F_2$ and $F_3$ selection criteria.

In 2012, the $F_{4:5}$ progeny rows were space-planted approximately 30.5-cm apart in two-row plots, 6.1 m longx 1.8 m wide. Progeny rows were selected based upon the same selection criteria as used during earlier generations. Individual progeny rows were bulked as pure-lines for subsequent preliminary yield tests. Georgia-1 BRU was designated as GA 122540 for further testing.

Yield, grade, and other agronomic traits were determined from randomized complete block designs using replicated field trials conducted for 5-yrs (2013-17) at multilocations in Georgia. Plots consisted of two-rows 6.1 m longx1.8 m wide with row spacing of 0.8 m within rows and 1.0 m between rows on adjacent plots. Tests were planted between mid-April and mid-May at 30.5 seed $cm^{-1}$. Production practices included conventional tillage, fertilization, recommended pesticides and rates, irrigated, and non-irrigated. These field trials were in a three-year rotation following cotton (*Gossypium* ssp.) and corn (*Zea mays* L.). Entries were dug near optimum maturity each year based upon hull-scrape determination from adjacent border plots (Williams and Drexler, Peanut Sci., 8:134-41, 1981).

Disease incidence of tomato spotted wilt virus (TSWV) was first assessed at midseason, when TSWV is usually the only disease occurring at this time during the growing season. Percentages (0-100%) of total disease (TD) incidence were scored prior to digging, which included primarily TSWV and any soilborne disease. A disease hit equaled a 30.5-cm section of row containing one or more symptomatic plants.

Visual leaf scorch ratings were taken at 85 days after planting (OAP) in 2016 and at 94 DAP in 2017. A 0-5 scale was used where 0=none (0%); 1=slight; 2=slight to moderate; 3=moderate; 4=moderate to severe; and 5=severe (>80%). Tests included maximum-input production practices of tillage, fertilization, recommended pesticides and rates, and irrigation; minimum-input production practices were approximately half the pesticides and no-irrigation; and no-pesticides and no-irrigation tests.

After digging and picking, pods were dried with forced warm air to 6% moisture. Pod samples were then hand-cleaned over a screen table before weighing for yield, shelling, and grading. In the grading process, total sound mature kernels (TSMK) equal the sum of sound mature kernels (SMK) and sound splits (SS). Sound mature kernels equals the percentage of sound mature seed excluding damaged and split seed riding a minimum slotted screen size of 6.35 mm in width. Dollar values were calculated upon USDA peanut loan schedules for each crop year, and were based upon yield and grade factors to obtain a gross dollar value return per hectare.

Data for each variable were subjected to analysis of variance (ANOVA). An LSD t-Test was used for two mean separations (Table 2), and Waller-Duncan's Bayesian t-Test (k-ratio=100) was used for mean separation involving three or more entries (Tables 3 and 4).

Example 2

Description of 'Georgia-18RU'

'Georgia-18RU' is unique from other runner-type peanut cultivars in having a combination of high level of TSWV resistance and leaf scorch resistance caused by *Leptosphaerulina crassiasca* (Séchet) Jackson and Bell, medium maturity, runner growth habit, prominent main stem, medium green foliage, medium-large runner seed size, and pink seedcoat color. Similar to other runner market types, it differs from the Virginia U.S. market type cultivars that also belong to the same subspecies and botanical variety by having smaller pods and seed size.

During the a five-year period (Table 2) when averaged over 34 tests at multiple locations in Georgia, 'Georgia- '18RU' was found to be the highest in TSMK grade and highest in number of seed per pound (smaller seed weight) compared to 'Georgia-06G'.

Also during two-years (2016-17) at multilocations in Georgia when planted early in mid-April (Tables 3 and 5) and when optimum planted in mid-May (Tables 4 and 6), 'Georgia-18RU' was among the highest in TSMK grade compared to all of the other runner genotypes tested both years. During 2016-17 in Tifton, Ga., Georgia-18RU was found to be among the lowest in leaf scorch ratings in maximum-input production tests, minimum-input production tests, and no-input production tests compared to several other runner and virginia genotypes, respectively (Tables 8 and 9).

'Georgia-18RU' is most similar to 'Georgia-06G'. Both of these peanut cultivars have similar normal-oleic fatty acid content, roasted flavor, blanchability, and maturity. However, 'Georgia-18RU' is distinctively different from 'Georgia-06G' in having a pink testa and more of a runner growth habit. 'Georgia-18RU is also distinct from 'Georgia-06G' in having higher percentage of total sound mature kernels (TSMK) (Tables 2-7). It also has a significantly smaller seed weight or higher seed count per pound compared to 'Georgia-06G' (Tables 2-6) which could save growers in seed cost at planting.

'Georgia-18RU' is distinct from several other runner and virginia-type peanut cultivars in having a very high-level of leaf scorch resistance (Tables 8 and 9). Leaf scorch is discussed by symptoms, causal organism, and disease cycle in the *Compendium of Peanut Diseases* ($1^{st}$ and $2^{nd}$ ed, 1984 and 1997, Amer. Phytopath. Soc.).

'Georgia-18RU' had among the highest pod yield and highest TSMK grade percentage when averaged over sixteen genotypes and eight UPPT locations (Table 7).

During 2017, Georgia-18RU was included in the Uniform Peanut Performance Tests (UPPT). When averaged across all U.S. test locations, 'Georgia-18RU' was found to be among the highest in pod yield and the highest in TSMK grade compared to 11 runner and five virginia type advanced breeding lines (Branch et al., 2018). These tests are annually conducted in Alabama, Florida, Georgia, North Carolina, Oklahoma, Texas, South Carolina, and Virginia.

During five-years (2013-17) averaged across 14 field tests in Georgia, 'Georgia-18RU' was found to have significantly ($P \le 0.05$) smaller percentage of large fancy pods than 'Georgia-06G'. 'Georgia-18RU' also had a higher percentage of pods than 'Georgia-06G' in the <13.49 mm but lower percentage of pods in the ≥13.49 mm size distribution using federals state inspection services (FSIS) pod presizer.

After pod presizing, the same pod samples were shelled according to FSIS standard procedures to determine shelling outturn. 'Georgia-18RU' was also found to have significantly ($P \le 0.05$) higher percentage of total sound mature kernels (TSMK) and medium kernels but similar percentage of jumbo, no. 1, and other kernels (OK), and damaged kernels (DK) as compared to 'Georgia-06G'. 'Georgia-18RU' was also found to have a higher percentage of total meat content than 'Georgia-06G'.

In summary, 'Georgia-18RU' was found to have high pod yields and low TSWV incidence similar to 'Georgia-06G'. It also was among the lowest in leaf scorch ratings compared to several other runner and virginia-type peanut genotypes. The combination of high levels of TSVW and leaf scorch resistance, high yield, and slightly smaller seed size compared to other large-seeded, runner-type cultivars currently being grown should be beneficial to peanut growers throughout the U.S.

Example 3

TABLE 2

FIVE-YEAR (34 TESTS) AVERAGE DISEASE INCIDENCE, POD YIELD, TSMK GRADE, SEED COUNT, AND DOLLAR VALUES OF 'GEORGIA-18RU' VS. 'GEORGIA-06G' AT MULTILOCATIONS IN GEORGIA, 2013-17.

| | Runner Cultivar | | | | | |
|---|---|---|---|---|---|---|
| | TSWV[†] (%) | TD[‡] (%) | Yield (lb/a) | TSMK[¶] (%) | Seed (no./lb) | Value ($/a) |
| 'Georgia-18RU' | 5 a* | 17 a | 5210 a | 79 a | 667 a | 1000 a |
| 'Georgia-06G' | 5 a | 16 a | 5351 a | 76 b | 625 b | 982 a |

*Within columns, means followed by the same letter are not significantly different at P ≤ 0.05.
[†]Percentage of tomato spotted wilt virus (TSWV) incidence at about mid-season.
[‡]Percentage of total disease (TD) incidence prior to digging, primarily TSWV and some soilborne diseases.
[¶]Percentage of total sound mature kernel (TSMK) grade equals all sound splits (SS) plus sound mature kernels (SMK) that ride a minimum slotted screen size of 16/64 × 3/4 inch for runner types.

Example 4

TABLE 3

FOUR-TEST AVERAGE PERFORMANCE WITH IRRIGATED MAXIMUM-INPUTS AND NONIRRIGATED MINIMUM-INPUTS OF 22 RUNNER AND 8 VIRGINIA-TYPE PEANUT GENOTYPE AT MULTILOCATIONS IN GEORGIA WHEN PLANTED IN MID-APRIL, 2016.

| | Peanut Genotype | | | | | |
|---|---|---|---|---|---|---|
| | TSWV (%) | TD (%) | Yield (lb/a) | TSMK (%) | Seed (no./lb) | Value ($/a) |
| | Runner-Types: | | | | | |
| Georgia-18RU | 5.4 ij* | 22.0 i-m | 4760 a | 78.4 a | 640 f-i | 897 a |
| Georgia-16HO | 6.8 g-j | 27.4 hij | 4732 ab | 76.3 a-e | 590 jkl | 866 ab |
| Georgia-06G | 4.9 j | 22.5 i-m | 4665 ab | 75.6 b-f | 610 ij | 855 abc |
| GA 122706 | 5.2 ij | 18.9 klm | 4504 a-d | 78.0 ab | 635 ghi | 848 a-d |
| TUFRunner '297' | 10.4 def | 30.6 gh | 4574 abc | 74.1 d-h | 568 kl | 819 a-e |
| GA 112557 | 4.5 j | 21.6 i-m | 4334 a-d | 78.5 a | 676 c-f | 814 a-e |
| Georgia-13M | 5.6 hij | 20.6 j-m | 4375 a-d | 76.6 a-d | 773 a | 806 a-e |
| Georgia Greener | 6.9 g-j | 27.4 hij | 4363 a-d | 75.8 b-f | 682 cde | 798 a-e |
| TUFRunner '511' | 14.6 bc | 48.2 bc | 4334 a-d | 75.8 b-f | 595 jk | 790 a-e |
| Georgia-12Y | 5.2 ij | 16.4 m | 4410 a-d | 72.9 ghi | 700 c | 777 a-e |

TABLE 3-continued

FOUR-TEST AVERAGE PERFORMANCE WITH IRRIGATED MAXIMUM-INPUTS AND NONIRRIGATED MINIMUM-INPUTS OF 22 RUNNER AND 8 VIRGINIA-TYPE PEANUT GENOTYPE AT MULTILOCATIONS IN GEORGIA WHEN PLANTED IN MID-APRIL, 2016.

| Peanut Genotype | TSWV (%) | TD (%) | Yield (lb/a) | TSMK (%) | Seed (no./lb) | Value ($/a) |
|---|---|---|---|---|---|---|
| Georgia-07W | 6.2 g-j | 27.8 ghi | 4240 a-d | 74.7 c-h | 606 ijk | 768 b-e |
| GA 122544 | 7.0 g-j | 23.9 h-l | 4155 a-e | 75.4 c-g | 652 e-h | 758 b-f |
| FloRun '107' | 13.9 bc | 44.9 cd | 4132 a-e | 74.2 d-h | 635 ghi | 742 c-g |
| TifNV-High O/L | 9.4 d-g | 24.2 h-k | 4155 a-e | 73.6 fgh | 614 hij | 740 c-g |
| Florida-07 | 10.4 def | 40.2 de | 4274 a-d | 71.0 ij | 604 ijk | 736 c-g |
| Georgia-09B | 8.2 f-I | 37.8 ef | 3966 c-h | 76.0 a-f | 690 cd | 726 d-h |
| Tifguard | 9.2 d-g | 29.8 gh | 3998 b-h | 72.6 hi | 660 d-g | 712 e-i |
| TUFRunner '727' | 14.9 b | 50.4 bc | 3958 c-h | 74.4 c-h | 616 hij | 711 e-j |
| GA 132713 | 5.8 hij | 20.4 j-m | 3933 d-h | 73.8 e-h | 744 ab | 702 e-j |
| FloRun '157' | 18.6 a | 61.2 a | 3915 d-h | 74.2 d-h | 709 bc | 700 e-j |
| GA 133108 | 6.2 g-j | 17.0 lm | 3539 e-i | 74.1 d-h | 776 a | 640 f-k |
| Georiga-14N | 6.6 g-j | 25.2 h-k | 3358 hi | 76.8 abc | 748 a | 623 g-k |
| Virginia-Types: | | | | | | |
| GA 132724 | 4.6 j | 20.0 klm | 4120 b-g | 75.0 c-h | 556 lm | 808 a-e |
| Georgia-11J | 7.5 f-j | 30.9 fgh | 4119 b-f | 69.4 jk | 409 p | 745 b-g |
| Florida Fancy | 14.5 bc | 54.1 b | 3486 f-i | 67.2 kl | 477 o | 609 h-k |
| CHAMPS | 13.9 bc | 50.5 bc | 3443 ghi | 68.4 jkl | 470 o | 608 h-k |
| Sullivan | 11.6 cde | 34.5 efg | 3396 ghi | 67.8 kl | 519 mn | 598 ijk |
| Wynne | 12.2 bcd | 40.2 de | 3440 ghi | 66.7 l | 423 p | 593 ijk |
| Bailey | 8.8 e-h | 30.1 gh | 3412 ghi | 67.0 kl | 490 no | 588 jk |
| Sugg | 13.8 bc | 51.6 bc | 2997 i | 67.2 kl | 469 o | 526 k |

*Within columns, means followed by the same letter are not significantly different at P ≤ 0.05.

Example 5

TABLE 4

SIX-TEST AVERAGE PERFORMANCE WITH AND WITHOUT IRRIGATION OF 23 RUNNER AND 7 VIRGINIA-TYPE PEANUT GENOTYPES AT MULTILOCATIONS IN GEORGIA WHEN PLANTED IN MID-MAY, 2016.

| Peanut Genotype | TSWV (%) | TD (%) | Yield (lb/a) | TSMK (%) | Seed (no./lb) | Value ($/a) |
|---|---|---|---|---|---|---|
| Runner Types: | | | | | | |
| TUFRunner '297' | 7.6 g-j* | 18.9 f-I | 5266 ab | 70.8 f-j | 634 mn | 910 ab |
| Georgia-13M | 3.5 op | 11.2 mno | 5113 abc | 72.8 c-f | 873 a | 908 a |
| Georgia-18RU | 4.4 l-p | 14.0 i-n | 4831 b-g | 75.8 a | 712 gh | 891 abc |
| GA 112557 | 5.6 j-o | 16.7 h-l | 4864 b-f | 75.1 ab | 732 fg | 890 a-d |
| Georgia-07W | 5.6 j-o | 14.2 i-n | 4960 a-e | 72.5 c-g | 689 h-k | 876 b-e |
| Georgia-16HO | 5.8 j-n | 17.8 g-j | 4950 b-e | 72.4 c-g | 663 klm | 876 b-e |
| TUFRunner '727' | 14.1 cd | 32.4 bc | 4941 b-e | 72.1 d-h | 697 hi | 872 b-f |
| TUFRunner '511' | 17.3 b | 37.3 b | 5004 a-d | 71.8 d-h | 650 lm | 870 b-f |
| Georgia-06G | 3.6 nop | 12.6 j-n | 4934 b-e | 72.4 c-g | 660 klm | 868 b-f |
| GA 122706 | 3.9 nop | 12.6 k-n | 4757 c-g | 74.5 abc | 735 fg | 861 b-f |
| GA 132713 | 5.1 k-p | 14.7 i-n | 4736 c-g | 71.7 e-I | 818 bc | 834 b-g |
| Florida-07 | 12.3 de | 30.3 cd | 4910 b-e | 69.4 i-l | 673 i-l | 833 b-g |
| Georgia-12Y | 4.1 nop | 12.0 k-o | 4764 c-g | 70.8 f-j | 740 fg | 821 c-h |
| Georgia-14N | 4.5 l-p | 16.1 h-m | 4532 e-i | 73.2 b-e | 831 b | 810 c-i |
| Georgia Greener | 6.5 i-m | 17.0 g-k | 4531 e-i | 72.8 c-f | 729 fg | 808 d-i |
| Georgia-09B | 7.1 h-k | 23.1 ef | 4611 d-h | 71.2 e-I | 773 de | 806 d-i |
| GA 133106 | 3.4 p | 7.4 o | 4417 g-j | 74.0 a-d | 696 hij | 801 e-i |
| FloRun '107' | 14.4 cd | 33.7 bc | 4679 c-g | 68.3 klm | 753 ef | 791 f-j |
| GA 122544 | 4.7 l-p | 11.8 l-o | 4438 f-j | 72.9 b-f | 686 h-k | 791 f-j |
| Tifguard | 6.5 i-l | 14.7 h-n | 4611 d-h | 69.8 h-l | 666 jkl | 790 f-j |
| TifNV-High O/L | 9.3 fg | 19.0 f-I | 4415 g-j | 69.8 h-l | 672 i-l | 752 g-k |
| FloRun '157' | 24.5 a | 48.7 a | 4212 h-j | 70.7 f-j | 789 cd | 731 i-l |
| GA 133108 | 4.6 l-p | 10.5 no | 4224 h-k | 70.3 g-k | 809 bc | 728 i-l |
| Virginia-Types: | | | | | | |
| Georgia-11J | 8.2 ghi | 22.0 efg | 5389 a | 68.6 jkl | 498 q | 964 a |
| GA 132724 | 4.3 m-p | 14.2 i-n | 4910 b-e | 71.8 d-h | 606 no | 910 ab |

TABLE 4-continued

SIX-TEST AVERAGE PERFORMANCE WITH AND WITHOUT IRRIGATION
OF 23 RUNNER AND 7 VIRGINIA-TYPE PEANUT GENOTYPES AT MULTILOCATIONS
IN GEORGIA WHEN PLANTED IN MID-MAY, 2016.

| | Peanut Genotype | | | | | |
|---|---|---|---|---|---|---|
| | TSWV (%) | TD (%) | Yield (lb/a) | TSMK (%) | Seed (no./lb) | Value ($/a) |
| Wynne | 9.4 fg | 27.0 de | 4433 f-j | 64.9 o | 500 q | 745 h-l |
| Sugg | 10.9 ef | 33.3 bc | 4059 jkl | 67.7 lmn | 516 q | 714 j-m |
| Bailey | 9.0 fgh | 19.9 fgh | 4132 i-l | 66.1 mno | 550 p | 706 klm |
| Sullivan | 11.8 e | 23.3 ef | 3942 kl | 64.9 o | 584 o | 664 lm |
| CHAMPS | 15.3 bc | 34.1 bc | 3742 l | 65.6 no | 522 pq | 635 m |

*Within columns, means followed by the same letter are not significantly different at $P \leq 0.05$.

Example 6

TABLE 5

FOUR-TESTS AVERAGE PERFORMANCE WITH IRRIGATED MAXIMUM-
INPUTS AND NONIRRIGATED NO-INPUTS OF 23 RUNNER AND
5 VIRGINIA-TYPE PEANUT GENOTYPE AT MULTILOCATIONS
IN GEORGIA WHEN PLANTED IN MID-APRIL, 2017.

| | Peanut Genotype | | | | | |
|---|---|---|---|---|---|---|
| | TSWV (%) | TD (%) | Yield (lb/a) | TSMK (%) | Seed (no./lb) | Value ($/a) |
| | Runner-Types: | | | | | |
| Georgia-06G | 4.1 hij* | 15.3 f-j | 5537 a | 77.7 e-h | 575 gh | 1025 a |
| GA 122706 | 3.6 ij | 14.2 f-j | 5234 ab | 80.4 a | 536 i | 1012 a |
| TUFRunner '297' | 7.8 cde | 28.6 bc | 5360 ab | 78.4 cde | 537 I | 1004 a |
| Georgia-07W | 4.5 f-j | 19.1 d-I | 5198 ab | 78.3 c-f | 582 fgh | 977 a |
| GA 122544 | 5.0 e-j | 15.5 f-j | 5168 abc | 78.7 cde | 614 def | 975 a |
| Georgia-09B | 3.8 ij | 20.3 d-h | 5180 abc | 78.3 c-f | 602 d-g | 975 a |
| Georgia-18RU | 3.4 ij | 20.6 d-g | 5029 a-d | 80.4 a | 602 d-g | 972 a |
| Georgia-16HO | 4.5 f-j | 14.8 f-j | 5120 a-d | 78.6 cde | 583 fgh | 968 a |
| FloRun '331' | 7.2 def | 24.4 cde | 5307 ab | 76.4 ij | 627 cd | 966 a |
| Georgia Greener | 4.5 f-j | 19.2 d-I | 5091 a-d | 78.0 d-g | 633 bcd | 955 a |
| Georgia-13M | 4.0 hij | 12.4 ij | 4970 a-d | 79.0 bcd | 667 ab | 944 ab |
| Tifguard | 6.7 d-h | 21.1 def | 5024 a-d | 77.0 ghi | 578 gh | 930 abc |
| GA 132712 | 4.2 g-j | 13.4 hij | 4871 a-e | 79.1 bc | 588 fgh | 922 abc |
| FloRun '107' | 9.2 cd | 28.9 bc | 4990 a-d | 76.8 hi | 590 e-h | 917 abc |
| GA 132705 | 3.8 ij | 10.8 j | 4875 a-e | 78.0 c-g | 603 d-g | 917 abc |
| TUFRunner '727' | 12.3 ab | 32.6 ab | 4890 a-d | 78.2 c-f | 561 hi | 916 abc |
| Georgia-12Y | 3.0 j | 13.6 hij | 4972 a-d | 76.3 ij | 622 cde | 912 abc |
| TifNV-High O/L | 6.0 e-I | 17.6 e-j | 4980 a-d | 76.3 ij | 566 hi | 908 abc |
| AU-NPL 17 | 7.0 d-g | 19.7 d-h | 4925 a-d | 75.4 j | 570 ghi | 888 a-d |
| TUFRunner '511 | 10.2 bc | 30.0 bc | 4722 a-e | 77.7 e-h | 557 hi | 882 a-d |
| Georiga-14N | 4.4 f-j | 14.7 f-j | 4565 b-e | 80.0 ab | 653 abc | 878 a-d |
| Florida-07 | 7.8 cde | 25.6 ed | 4842 a-e | 75.6 j | 580 gh | 877 a-d |
| FloRun '157' | 14.5 a | 38.9 a | 4790 a-e | 76.4 ij | 680 a | 874 a-d |
| | Virginia-Types: | | | | | |
| GA 132724 | 4.4 f-j | 17.6 e-j | 4767 a-e | 77.3 f-I | 478 j | 941 ab |
| Georgia-11J | 5.0 e-j | 13.7 g-j | 4809 a-e | 74.3 k | 349 l | 933 ab |
| Wynne | 6.7 d-h | 25.3 cd | 4280 cde | 71.4 l | 415 k | 786 bcd |
| Sullivan | 5.8 e-j | 17.7 e-j | 4213 de | 70.8 l | 492 j | 767 cd |
| Bailey | 7.0 d-g | 23.2 cde | 3970 e | 71.2 l | 487 j | 726 d |

*Within columns, means followed by the same letter are not significantly different at $P \leq 0.05$.

Example 7

TABLE 6

SIX-TEST AVERAGE PERFORMANCE WITH AND WITHOUT IRRIGATION OF 22 RUNNER AND 6 VIRGINIA-TYPE PEANUT GENOTYPES AT MULTILOCATIONS IN GEORGIA WHEN PLANTED IN MID-MAY, 2017.

| Peanut Genotype | TSWV (%) | TD (%) | Yield (lb/a) | TSMK (%) | Seed (no./lb) | Value ($/a) |
|---|---|---|---|---|---|---|
| Runner Types: | | | | | | |
| TUFRunner '297' | 9.8 c* | 15.3 c | 5532 a | 74.9 de | 600 l | 1008 a |
| Georgia-06G | 2.8 I | 6.1 j | 5524 a | 75.2 cd | 620 kl | 1005 ab |
| Georgia-16HO | 4.2 ghi | 8.7 ghi | 5540 a | 73.7 efg | 644 ijk | 994 abc |
| FloRun '331' | 9.5 c | 14.9 cd | 5582 a | 73.0 gh | 702 de | 990 abc |
| GA 122706 | 3.7 hi | 6.5 ij | 5277 a-d | 76.8 ab | 671 ghi | 983 abc |
| Georgia-18RU | 3.2 I | 8.3 hij | 5257 a-d | 77.0 a | 672 fgh | 982 abc |
| Georgia-12Y | 3.8 ghi | 7.3 hij | 5520 a | 72.9 gh | 688 efg | 976 abc |
| Georgia-13M | 3.9 ghi | 7.9 hij | 5305 abc | 75.6 bcd | 798 a | 974 a-d |
| Georgia-09B | 3.7 hi | 11.4 ef | 5377 ab | 73.7 efg | 678 e-h | 962 a-e |
| Georgia Greener | 5.9 ef | 9.1 fgh | 5280 a-d | 74.8 de | 682 e-h | 959 a-f |
| GA 132705 | 3.5 I | 6.0 j | 5141 a-e | 74.9 de | 700 e | 938 a-f |
| AU-NPL 17 | 8.8 cd | 14.4 cd | 5287 a-d | 72.6 gh | 659 hij | 934 a-f |
| FloRun '107' | 12.8 b | 21.4 ab | 5166 a-e | 72.0 h | 729 cd | 909 a-g |
| TifNV-High O/L | 8.3 cd | 12.6 de | 5044 a-e | 73.0 gh | 630 k | 896 b-h |
| GA 132712 | 3.5 I | 7.4 hij | 4757 c-f | 76.6 ab | 698 ef | 887 c-h |
| FloRun '157' | 16.3 a | 23.9 a | 4784 b-f | 74.3 def | 733 c | 867 d-i |
| TUFRunner '511' | 13.7 b | 21.0 b | 4698 def | 75.1 cd | 634 jk | 854 e-j |
| Georgia-14N | 3.1 I | 7.8 hij | 4598 ef | 76.3 abc | 771 b | 852 f-j |
| Tifguard | 7.2 de | 10.9 efg | 4590 ef | 73.4 fg | 628 k | 817 g-k |
| GA 122544 | 5.5 efg | 7.7 hij | 4375 f | 75.0 d | 673 fgh | 792 h-k |
| Georgia-07W | 5.3 fgh | 9.3 fgh | 4318 f | 75.0 d | 663 ghi | 789 h-k |
| Florida-07 | 12.9 b | 19.8 b | 4344 f | 73.3 fg | 677 e-h | 776 ijk |
| Virginia-Types: | | | | | | |
| Florida Fancy | 8.8 cd | 15.5 c | 5232 a-d | 72.7 gh | 544 m | 961 a-f |
| GA 132724 | 3.8 ghi | 7.6 hij | 5197 a-d | 74.3 def | 553 m | 953 a-f |
| Georgia-11J | 9.6 c | 14.5 cd | 5060 a-e | 72.7 gh | 478 o | 931 a-f |
| Emery | 9.6 c | 21.5 ab | 4390 f | 70.3 I | 473 o | 776 ijk |
| Bailey | 6.4 ef | 14.4 cd | 4267 f | 69.2 ij | 514 n | 749 jk |
| Wynne | 9.6 c | 20.4 b | 4192 f | 68.6 j | 463 o | 724 k |

*Within columns, means followed by the same letter are not significantly different at P ≤ 0.05.

Example 8

TABLE 7

MEAN PERFORMANCE OF 2017 UPPT FOR BREEDING LINES AND CHECKS ACROSS ALL LOCATIONS IN THE U.S.

| | Type/Line | | | |
|---|---|---|---|---|
| | Pod Yield lb/A | Yield Rank | Fancy Pods % | TSMK % |
| Runner lines | 5230$^{ns*}$ | — | 40.1$^{\beta}$ | 73.0$^{\beta}$ |
| Georgia-06G (ck) | 5837$^a$ | 2 | 48.0$^c$ | 74.9$^{bc}$ |
| ARSOK-R47A | 5039$^{bcd}$ | 12 | 13.3$^{fg}$ | 73.8$^{bcd}$ |
| Georgia-18RU | 5851$^a$ | 1 | 21.0$^{ef}$ | 77.2$^a$ |
| GA 122544 | 5272$^{a-d}$ | 9 | 33.8$^d$ | 74.4$^{bc}$ |
| GA 132724 | 5204$^{a-d}$ | 10 | 75.0$^b$ | 74.8$^{bc}$ |
| TxL 080256-02 | 5006$^{bcd}$ | 13 | 23.7$^e$ | 71.7$^{efg}$ |
| TxL 090105-07 | 4111$^e$ | 16 | 77.8$^{ab}$ | 68.6$^{hij}$ |
| TxL 090206-41 | 4551$^{de}$ | 15 | 83.6$^{ab}$ | 66.8$^j$ |
| UF 07024-2-10-1 | 5551$^{ab}$ | 5 | 25.2$^{de}$ | 73.4$^{cde}$ |
| UF 09x58-3-3-2 | 5522$^{ab}$ | 6 | 10.5$^g$ | 72.1$^{def}$ |
| UF 10x09-3-4-1-1 | 5587$^{ab}$ | 3 | 29.2$^{de}$ | 75.1$^{bc}$ |
| Virginia lines | 5248$^{ns}$ | — | 78.1$^a$ | 71.2$^a$ |
| Bailey (ck) | 5423$^{abc}$ | 8 | 74.7$^b$ | 70.3$^{fgh}$ |
| ARSOK-V85-377 | 5041$^{bcd}$ | 11 | 75.6$^b$ | 71.7$^{efg}$ |
| ARSOK-V85-7 | 4718$^{cde}$ | 14 | 78.2$^{ab}$ | 75.5$^{ab}$ |
| N12008olCLSmT | 5492$^{ab}$ | 7 | 76.7$^{ab}$ | 70.1$^{ghi}$ |
| N13048 + ol | 5568$^{ab}$ | 4 | 85.3$^a$ | 68.2$^{ij}$ |
| Mean | 5257 | | 52.4 | 72.5 |
| CV (%) | 13.7 | | 17.4 | 2.7 |

*Within columns, means followed by the same letter are not significantly different at P ≤ 0.05.

Example 9

Leaf Scorch Analysis

TABLE 8

2016 Average Leaf Scorch Rating (0-5 scale) among 22 Runner and 8 Virginia-Type Peanut Genotypes under Maximum and Minimum Input Tests at the Coastal Plain Experiment Station, Tifton, GA.[†]

| Peanut Genotype | Max. Test | Min. Test | Mean |
|---|---|---|---|
| Runner-type | | | |
| Tifguard | 4.8 a* | 3.4 a | 4.1 a |
| GA 133108 | 4.4 ab | 3.0 ab | 3.7 b |
| Georgia-14N | 4.2 b | 2.8 b | 3.5 b |
| TifNV-High O/L | 3.4 c | 3.4 a | 3.4 b |
| GA 122544 | 3.2 c | 1.4 cde | 2.3 c |
| Florida-07 | 1.8 de | 1.8 c | 1.8 d |
| Georgia-09B | 1.8 de | 1.6 cd | 1.7 de |
| TUFRunner '727' | 2.0 d | 1.4 cde | 1.7 de |
| Georgia Greener | 1.8 de | 1.4 cde | 1.6 def |
| Georgia-12Y | 1.4 ef | 1.6 cd | 1.5 d-g |
| TUFRunner '297' | 1.4 ef | 1.4 cde | 1.4 e-h |
| FloRun '107' | 0.8 ghi | 1.8 c | 1.3 f-I |
| GA 112557 | 0.8 ghi | 1.6 c d | 1.2 g-j |
| FloRun '157' | 1.2 fg | 1.0 efg | 1.1 h-k |
| Georgia-16HO | 1.0 fgh | 1.0 efg | 1.0 i-l |
| Georgia-07W | 0.8 ghi | 1.2 def | 1.0 i-l |
| GA 122706 | 0.6 hij | 1.0 efg | 0.8 klm |
| TUFRunner '511' | 0.8 ghi | 0.8 fgh | 0.8 klm |
| Georgia-06G | 0.6 hij | 1.0 efg | 0.8 klm |
| GA 132713 | 0.4 ijk | 1.0 efg | 0.7 lmn |
| Georgia-13M | 0.2 jk | 0.6 ghi | 0.4 no |
| Georgia-18RU | 0.0 k | 0.2 i | 0.1 o |
| Virginia-type | | | |
| Florida Fancy | 1.4 ef | 1.4 cde | 1.4 e-h |
| GA 132724 | 1.4 ef | 1.4 cde | 1.4 e-h |
| Sugg | 1.4 ef | 1.0 efg | 1.2 g-j |
| Wynne | 1.0 fgh | 1.2 def | 1.1 h-k |
| Bailey | 0.8 ghi | 1.0 efg | 0.9 jkl |
| CHAMPS | 0.6 hij | 1.0 efg | 0.8 klm |
| Sullivan | 0.2 jk | 0.8 fgh | 0.5 mn |
| Georgia-11J | 0.6 hij | 0.4 hi | 0.5 mn |

[†]Leaf Scorch Visual Rating: 0 = None (0%); 1 = slight; 2 = slight - moderate; 3 = moderate; 4 = moderate - severe; and 5 = severe (>80%) at 85 days after planting.
*Means within the same column followed by the same letter are not significantly different at $P \leq 0.05$.

TABLE 9

2017 Average Leaf Scorch Rating (0-5 scale) among 23 Runner and 5 Virginia-Type Peanut Genotypes under Maximum and No-Input Tests at the Coastal Plain Experiment Station, Tifton, GA.[†]

| Peanut Genotype | Max. Test | No Test | Mean |
|---|---|---|---|
| Runner-type | | | |
| Tifguard | 4.0 a* | 2.2 a | 3.1 a |
| TifNV-High O/L | 3.5 ab | 2.2 a | 2.9 a |
| Georgia-14N | 3.0 bcd | 1.2 b | 2.1 b |
| AU-NPL 17 | 3.2 bc | 0.8 bcd | 2.0 bc |
| Georgia-09B | 2.8 cde | 1.0 bc | 1.9 bcd |
| Florida-07 | 2.5 def | 1.0 bc | 1.8 b-e |
| Georgia Greener | 2.8 cde | 0.5 cde | 1.6 b-e |
| Georgia-07W | 2.5 def | 0.5 cde | 1.5 c-f |
| GA 122544 | 2.8 cde | 0.2 de | 1.5 c-f |
| FloRun '107' | 2.2 efg | 0.5 cde | 1.4 d-g |
| Georgia-06G | 2.0 fgh | 0.5 cde | 1.2 e-h |
| Georgia-12Y | 2.2 efg | 0.2 de | 1.2 e-h |
| TUFRunner '727' | 1.5 hij | 1.0 bc | 1.2 e-h |
| FloRun '157' | 1.5 hij | 0.5 cde | 1.0 f-I |
| TUFRunner '297' | 1.5 hij | 0.5 cde | 1.0 f-I |
| FloRun '331' | 1.5 hij | 0.2 de | 0.9 ghi |
| GA 122706 | 1.8 ghi | 0.0 e | 0.9 ghi |
| TUFRunner '511' | 1.2 ij | 0.2 de | 0.8 hij |
| Georgia-16HO | 1.2 ij | 0.0 e | 0.6 ijk |
| GA 132712 | 1.0 jk | 0.0 e | 0.5 ijk |
| GA 132705 | 1.0 jk | 0.0 e | 0.5 ijk |
| Georgia-13M | 0.5 kl | 0.0 e | 0.2 jk |
| Georgia-18RU | 0.2 l | 0.0 e | 0.1 k |
| Virginia-type | | | |
| GA 132724 | 3.2 bc | 0.5 cde | 1.9 bcd |
| Bailey | 1.8 ghi | 1.0 bc | 1.4 d-g |
| Wynne | 1.8 ghi | 0.8 bcd | 1.2 e-h |
| Sullivan | 1.0 jk | 0.2 de | 0.6 ijk |
| Georgia-11J | 0.2 l | 0.0 e | 0.1 k |

[†]Leaf Scorch Visual Rating: 0 = None (0%); 1 = slight; 2 = slight - moderate; 3 = moderate; 4 = moderate - severe; and 5 = severe (>80%) at 94 days after planting.
*Means within the same column followed by the same letter are not significantly different at $P \leq 0.05$.

Example 10

Pod Size Distribution

Pod size distribution is an important shelling characteristic of peanut cultivars. Peanut pods are processed through different stages of shelling based upon the pod size distribution. 'Georgia-18RU' has a significantly smaller percentage of fancy pods than 'Georgia-06G' (Table 10).

TABLE 10

FIVE-YEAR (14 TESTS) AVERAGE POD PRESIZER DISTRIBUTION OF 'GEORGIA-18RU' VS. 'GEORGIA-O6G', 2013-17.

| Runner Cultivar | Fancy Pods‡ (%) | $+^{38}/_{64}''$ (%) | $-38 + ^{34}/_{64}''$ (%) | $-^{34}/_{64}''$ (%) |
|---|---|---|---|---|
| Georgia-18RU | 23 b* | 1 b | 22 b | 77 a |
| Georgia-O6G | 62 a | 5 a | 57 a | 38 b |

*Within columns, means followed by the same letter are not significantly different at $P \leq 0.05$.

‡Fancy Pods = $+^{38}/_{64}$ and $+^{34}/_{64}$ inches summed together.

Example 11

Production of 'Georgia-18RU' Plants

'Georgia-18RU' can be grown under normal conditions for growing peanuts, and bulk seed for large-scale planting can be obtained by methods known in certified seed production. For example, bulk seed may be produced by planting 'Georgia-18RU' seeds (such as those obtained from ATCC Accession No: PTA-127083), allowing the mature plants to produce seed by self-pollination with each other and then collecting the seed. Standard precautions should be taken to prevent cross-pollination from other peanut plants, such as growing the variety in an isolated plot of sterilized soil, removing adjacent vegetation, etc. The 'Georgia-18RU' seeds deposited with ATCC are breeder seeds; propagation of plants from these seeds can be performed under standard conditions.

Example 12

Introducing Traits of 'Georgia-18RU' into Other Peanut Varieties

The morphological and physiological characteristics of 'Georgia-18RU', including resistance to diseases that affect peanuts (including TSWV and leaf scorch caused by *Leptosphaerulina crassiasca* (Sechet) Jackson and Bell) as well as high percentage of total sound mature kernels (TSMK), small seed weight, high pod yield, small percentage of large fancy pods (e.g., ≥13.49 mm size distribution), high percentage of total meat content, medium maturity, runner growth habit, prominent main stem, medium green foliage, medium-large runner seed size, pink seedcoat (testa) color, or combinations thereof, can be introduced into other peanut varieties (such as other peanut cultivars) by conventional breeding techniques. For example, 'Georgia-18RU' can be grown in pollination proximity to another variety of peanut, allowing cross-pollination to occur between 'Georgia-18RU' and the other variety, and then harvesting the hybrid seeds. Plants grown from these hybrid seeds can then be tested for the maintenance of the characteristics described herein for 'Georgia-18RU' (such as one or more of TSWV resistance, leaf scorch resistance caused by *Leptosphaerulina crassiasca* (Sechet) Jackson and Bell, high percentage of total sound mature kernels (TSMK), small seed weight, high pod yield, small percentage of large fancy pods (e.g., ≥13.49 mm size distribution), high percentage of total meat content, medium maturity, runner growth habit, prominent main stem, medium green foliage, medium-large runner seed size, pink seedcoat (testa) color, or combinations thereof), and/or the plants can simply be observed to see if they display the same characteristics of 'Georgia-18RU', such as those described in Tables 2-10.

For example, plants grown from these hybrid seeds can be tested for any of the morphological characteristics described herein, for example TSWV resistance, leaf scorch resistance caused by *Leptosphaerulina crassiasca* (Sechet) Jackson and Bell, high percentage of total sound mature kernels (TSMK), small seed weight, high pod yield, small percentage of large fancy pods (e.g., ≥13.49 mm size distribution), high percentage of total meat content, medium maturity, runner growth habit, prominent main stem, medium green foliage, medium-large runner seed size, pink seedcoat (testa) color, or combinations thereof. In this way, TSWV resistance, leaf scorch resistance caused by *Leptosphaerulina crassiasca* (Sechet) Jackson and Bell, high percentage of TSMKs, small seed weight, high pod yield, small percentage of large fancy pods (e.g., ≥13.49 mm size distribution), high percentage of total meat content, medium maturity, runner growth habit, prominent main stem, medium green foliage, medium-large runner seed size, pink seedcoat (testa) color, or combinations thereof, may be combined with other desirable plant characteristics. Thus, the provision of 'Georgia-18RU' enables the production of progeny plants of 'Georgia-18RU' having one or more of TSWV resistance, leaf scorch resistance caused by *Leptosphaerulina crassiasca* (Sechet) Jackson and Bell, and a high percentage of TSMKs, and in some examples all of these, and in some examples also one or more of small seed weight, high pod yield, small percentage of large fancy pods (e.g., ≥13.49 mm size distribution), high percentage of total meat content, medium maturity, runner growth habit, prominent main stem, medium green foliage, medium-large runner seed size, pink seedcoat (testa) color. "Progeny plants" of 'Georgia-18RU' are any plants that are the offspring of a cross between 'Georgia-18RU' and any other plant or plants. Progeny plants also include successive generations of the offspring, for example those selected for TSWV resistance, leaf scorch resistance caused by *Leptosphaerulina crassiasca* (Sechet) Jackson and Bell, high yield, and a high percentage of TSMKs. First-generation progeny plants may retain the properties of the 'Georgia-18RU' parent (such as TSWV resistance, leaf scorch resistance caused by *Leptosphaerulina crassiasca* (Sechet) Jackson and Bell, high yield, and a high percentage of TSMKs). However, if a first-generation progeny plant does not retain the characteristics observed with 'Georgia-18RU' (such as TSWV resistance, leaf scorch resistance caused by *Leptosphaerulina crassiasca* (Sechet) Jackson and Bell, high yield, and a high percentage of TSMKs), subsequent generations of offspring can be recycled for those which have at least the same TSWV resistance, leaf scorch resistance caused by *Leptosphaerulina crassiasca* (Sechet) Jackson and Bell, yield, and percentage of TSMKs as does 'Georgia-18RU' described herein. In one embodiment, subsequent generations of offspring can have TSWV resistance, leaf scorch resistance caused by *Leptosphaerulina crassiasca* (Sechet) Jackson and Bell, yield, and percentage of TSMKs similar to that or even that exceed that of 'Georgia-18RU'.

In addition, 'Georgia-18RU' can be used as transformation targets for the production of transgenic peanuts. In certain embodiments, the present disclosure contemplates the transformation of cells derived from 'Georgia-18RU' with at least one transgene. For example, transgenes that can be used, include, but are not limited to, transgenes that confer: resistance to one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination, abiotic stress tolerance, modified phosphorus content, modified antioxidant content; modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, and modified pod color. Examples of such genes and methods of transforming plants are described in U.S. Pat. No. 6,025,545.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

I claim:

1. A seed of peanut variety 'Georgia-18RU', wherein a representative sample of seed of the variety has been deposited under American Type Culture Collection (ATCC) Accession No. PTA-127083.

2. A seed mixture, comprising the seed of claim 1.

3. A peanut plant of peanut variety 'Georgia-18RU', wherein a representative sample of seed of the variety has been deposited under ATCC Accession No. PTA-127083.

4. A plant part of the peanut plant of claim 3.

5. The plant part of claim 4, wherein the plant part is pollen, an ovule or a cell.

6. A tissue culture produced from protoplasts or cells from the peanut plant of claim 3.

7. The tissue culture of claim 6, wherein the cells or protoplasts are produced from a leaf, stem, protoplast, pollen, ovule, embryo, cotyledon, hypocotyl, meristematic cell, root, root tip, pistil, anther, flower, seed, shoot, stem, pedicel, pod or petiole.

8. A peanut plant regenerated from the tissue culture of claim 7, wherein the peanut plant comprises all of the morphological and physiological properties of a peanut plant grown from a seed of peanut variety 'Georgia-18RU', wherein a representative sample of seed of the variety has been deposited under ATCC Accession No. PTA-127083.

9. A method of producing peanut seed, comprising:
crossing the peanut plant of claim 3 with itself or a second peanut plant; and
harvesting a resulting peanut seed.

10. A peanut seed produced by the method of claim 9.

11. A peanut plant, or a part thereof, produced by growing the seed of claim 10.

12. The method of claim 9, wherein the second peanut plant is transgenic.

13. An $F_1$ hybrid seed produced by the method of claim 9.

14. A method of producing a plant of peanut variety 'Georgia-18RU' comprising an added desired trait, comprising:
transforming a transgene conferring a desired trait into the plant of claim 3, thereby producing a plant of peanut variety 'Georgia-18RU' comprising the added desired trait.

15. The method of claim 14, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination, abiotic stress tolerance, modified phosphorus content, modified antioxidant content; modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, or modified pod color.

16. The method of claim 15, wherein the desired trait is disease resistance and the resistance is southern stem rot, late leaf spot, cylindrocladium black rot, sclerotinia blight, early leaf spot, tomato spotted wilt virus, or pod rot complex;
insect resistance and the insect resistance is to thrips, southern corn rootworm, burrowing bug, lesser cornstalk borer, leaf hopper, aphid, or nematode;
modified fatty acid content and the fatty acid is one or more of oleic acid, linoleic acid, and palmitic acid; and/or
modified fatty acid content which confers improved oil stability and resistance to oxidative degradation.

17. The method of claim 15, wherein the resistance to an insect is conferred by a transgene encoding a *Bacillus thuringiensis* (Bt) endotoxin.

18. The method of claim 15, wherein the herbicide tolerance comprises tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, and chlorophenoxy acetic acid.

19. A plant produced by the method of claim 14.

20. A method of introducing a desired trait into peanut variety 'Georgia-18RU' comprising:
(a) crossing the plant of claim 3 with a second plant comprising a desired trait to produce $F_1$ progeny plants;
(b) selecting $F_1$ progeny plants that have the desired trait to produce selected $F_1$ progeny plants;
(c) crossing the selected progeny plants with at least a first plant of variety 'Georgia-18RU' to produce backcross progeny plants;
(d) selecting backcross progeny plants that have the desired trait and physiological and morphological characteristics of peanut variety 'Georgia-18RU' to produce selected backcross progeny plants; and
(e) repeating steps (c) and (d) one or more times in succession to produce selected second or higher backcross progeny plants that comprise the desired trait and the physiological and morphological characteristics of peanut variety 'Georgia-18RU' when grown in the same environmental conditions.

21. The method of claim 20, wherein the desired trait comprises one or more of herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus content, modified antioxidant content, modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, and modified pod color.

22. A peanut plant of peanut variety 'Georgia-18RU', wherein a representative sample of seed of the variety has been deposited under ATCC Accession No. PTA-127083, further comprising a single locus conversion.

23. The plant of claim 22, wherein the single locus conversion is introduced into the plant by backcrossing or genetic transformation.

24. A peanut plant produced by transforming the peanut plant of claim 22 with a transgene that confers a desired trait, wherein the desired trait is one or more of herbicide tolerance, resistance to an insect, resistance to a bacterial disease, resistance to a viral disease, resistance to a fungal disease, resistance to a nematode, resistance to a pest, male sterility, site-specific recombination, abiotic stress tolerance, modified phosphorus content, modified antioxidant content, modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, and modified pod color.

25. A method of producing a hybrid peanut plant derived from peanut variety 'Georgia-18RU', comprising:
   (a) preparing a progeny plant derived from peanut variety 'Georgia-18RU' ATCC Accession No. by crossing the plant of claim 3 with a peanut plant of a second variety;
   (b) crossing the progeny plant with itself or a second plant to produce a seed of a progeny plant of a subsequent generation;
   (c) growing a progeny plant of a subsequent generation from said seed and crossing the progeny plant of a subsequent generation with itself or a second plant; and
   (d) repeating steps (b) and (c) for an additional 3-10 generations with sufficient inbreeding to produce a hybrid peanut plant derived from the peanut variety 'Georgia-18RU'.

26. An $F_1$ plant produced by the method of claim 25.

27. A method of producing a commodity plant product comprising:
   obtaining the peanut plant of claim 3 or a part thereof; and producing the commodity plant product therefrom.

28. The method of claim 27, wherein the commodity plant product is protein concentrate, protein isolate, peanut oil, peanut butter, roasted peanuts, salted peanuts, livestock feed, peanut flour, soaps, and/or plastics.

* * * * *